US008609717B2

(12) United States Patent
KC et al.

(10) Patent No.: US 8,609,717 B2
(45) Date of Patent: Dec. 17, 2013

(54) β- AND γ-DIKETONES AND γ-HYDROXYKETONES AS *WNT*/β-CATENIN SIGNALING PATHWAY ACTIVATORS

(75) Inventors: Sunil Kumar KC, San Diego, CA (US); David Mark Wallace, San Diego, CA (US); John Hood, San Diego, CA (US); Charlene F. Barroga, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 93 days.

(21) Appl. No.: 13/211,665

(22) Filed: Aug. 17, 2011

(65) Prior Publication Data
US 2012/0046320 A1  Feb. 23, 2012

Related U.S. Application Data

(60) Provisional application No. 61/374,687, filed on Aug. 18, 2010, provisional application No. 61/427,974, filed on Dec. 29, 2010.

(51) Int. Cl.
*C07D 319/18* (2006.01)
*A61K 31/357* (2006.01)

(52) U.S. Cl.
USPC ........... 514/452; 514/456; 514/465; 549/362; 549/405; 549/436

(58) Field of Classification Search
None
See application file for complete search history.

(56) References Cited

U.S. PATENT DOCUMENTS

| | | |
|---|---|---|
| 3,855,675 A | 12/1974 | Denzel et al. |
| 4,032,526 A | 6/1977 | Cross et al. |
| 4,284,629 A | 8/1981 | Grohe et al. |
| 4,537,617 A | 8/1985 | Plath et al. |
| 4,761,471 A | 8/1988 | Urist |
| 5,194,619 A | 3/1993 | Reuschling et al. |
| 6,020,488 A | 2/2000 | Wuonola et al. |
| 6,624,184 B1 | 9/2003 | Gu et al. |
| 7,041,837 B2 | 5/2006 | Lohray et al. |
| 7,053,111 B2 | 5/2006 | Gu et al. |
| 7,060,720 B2 | 6/2006 | Gu et al. |
| 7,205,324 B2 | 4/2007 | Gu et al. |
| 2004/0266732 A1 | 12/2004 | Galvez et al. |
| 2005/0267110 A1 | 12/2005 | Hirano et al. |
| 2005/0282707 A1 | 12/2005 | Almsick et al. |
| 2006/0142358 A1 | 6/2006 | Autier et al. |
| 2006/0276536 A1 | 12/2006 | Vander Jagt et al. |
| 2007/0060644 A1 | 3/2007 | Vander Jagt et al. |
| 2008/0139585 A1 | 6/2008 | Rathinavelu et al. |
| 2008/0146555 A1 | 6/2008 | Caligiuri et al. |
| 2009/0232754 A1 | 9/2009 | Meyer et al. |
| 2010/0152493 A1 | 6/2010 | Shibata et al. |

FOREIGN PATENT DOCUMENTS

| | | |
|---|---|---|
| EP | 0230110 | 7/1987 |
| EP | 0290442 | 11/1988 |
| EP | 0322033 | 6/1989 |
| EP | 0360701 | 8/1989 |
| EP | 0365089 | 10/1989 |
| EP | 0500005 | 8/1992 |
| EP | 0885869 | 12/1998 |
| EP | 1067195 | 1/2001 |
| JP | 2008106011 | 5/2008 |
| JP | 2008222606 | 9/2008 |
| JP | 2010195768 | 9/2010 |
| WO | WO/87/05297 | 9/1987 |
| WO | WO8803805 | 6/1988 |
| WO | WO/90/11366 | 10/1990 |
| WO | WO9322259 | 11/1993 |
| WO | WO9632938 | 10/1996 |
| WO | WO9640668 | 12/1996 |
| WO | WO0026197 | 5/2000 |
| WO | WO0104100 | 1/2001 |
| WO | WO0119822 | 3/2001 |
| WO | WO0127116 | 4/2001 |
| WO | WO0177090 | 10/2001 |
| WO | WO/01/53268 | 1/2002 |
| WO | WO0243675 | 6/2002 |
| WO | WO03009841 | 2/2003 |
| WO | WO03016266 | 2/2003 |
| WO | WO/2005/009997 | 2/2005 |
| WO | WO2005108347 | 11/2005 |
| WO | WO2006017896 | 2/2006 |
| WO | WO2006077851 | 7/2006 |
| WO | WO2007051314 | 5/2007 |
| WO | WO2007059108 | 5/2007 |
| WO | WO2008118626 | 10/2008 |

(Continued)

OTHER PUBLICATIONS

Wu et al., Toxicology, 236, pp. 1-6, 2007.*
Chemical Abstracts 154:83772 of Wang et al, Natural Product Communications (2009), 4(11), pp. 1571-1574.*
Biftu et al, Journal of the Chemical Society, Perkin Transactions 1: Organic and Bio-Organic Chemistry (1972-1999), (1978), vol. 19, pp. 1147-1150.*
Wang et al, Biochemistry, (2001), 40(8), pp. 2511-2521.*
Wang et al, Natural Product Communications (2009), 4(11), pp. 1571-1574.*

(Continued)

*Primary Examiner* — Zinna Northington Davis
(74) *Attorney, Agent, or Firm* — Fish & Richardson P.C.

(57) ABSTRACT

The present invention discloses β-diketones, γ-diketones or γ-hydroxyketones or analogs thereof, that activate Wnt/β-catenin signaling and thus treat or prevent diseases related to signal transduction, such as osteoporosis and osteoarthropathy; osteogenesis imperfecta, bone defects, bone fractures, periodontal disease, otosclerosis, wound healing, craniofacial defects, oncolytic bone disease, traumatic brain injuries related to the differentiation and development of the central nervous system, comprising Parkinson's disease, strokes, ischemic cerebral disease, epilepsy, Alzheimer's disease, depression, bipolar disorder, schizophrenia; eye diseases such as age related macular degeneration, diabetic macular edema or retinitis pigmentosa and diseases related to differentiation and growth of stem cell, comprising hair loss, hematopoiesis related diseases and tissue regeneration related diseases.

16 Claims, No Drawings

(56) References Cited

FOREIGN PATENT DOCUMENTS

| WO | WO2009071997 | 6/2009 |
|---|---|---|
| WO | WO2009129267 | 10/2009 |
| WO | WO2009136889 | 11/2009 |
| WO | WO2010054126 | 5/2010 |
| WO | WO 2012/106343 | 8/2012 |

OTHER PUBLICATIONS

Selic et al., "A Simple Stereoselective One-Pot Conversion of Compounds with a Dimethylaminomethylene Group into Enol Esters," *Synthetic Communications*, vol. 31, No. 11 (2001) pp. 1743-1752.
Benati et al., "Thermal reactions of aryl azides with trans-1,2-dibenzoyl- and trans-1,2-diacetyl-ethylene. Reactivity of 4,5-dibenzoyl- and 4,5-diacetyl-1-aryltriazolines" *J. Chem. Soc.*, Perkin Trans. 1, No. 12 (1989), pp. 2235-2243.
Jończyk et al., "Reactions of carbanions from 2-(dialkylamino)-arylacetonitriles with acetylene—simple syntheses of 1,3-dienamines and 1,4-diketones[1]," *Tetrahedron*, vol. 46, No. 3 (1990), pp. 1025-1038.
Li et al., "Ring-Opening of Tertiary Cyclopropanols Derived from β-Diketones," *Tetrahedron*, vol. 62, (2002) pp. 7762-7771.
Nevar et al., "One Step Preparation of 1,4-Diketones from Methyl Ketones and α-Bromomethyl Ketones in the Presence of $ZnCl_2$ • t-BuOH • $Et_2$ NR as a Condensation Agent" *Synthesis*, No. 9 (2000), pp. 1259-1262.
Nishiyama and Kobayashi, "Synthesis of 1,4-Diketones: Reaction of α-Bromo Ketones with Tetrakis (dimethylamino)ethylene (TDAE)," *Tetrahedron Letters*, vol. 47, (2006) pp. 5565-5567.
Rosa et al., "N-and C-Acylation in β-Enamino Ketones : Structural Effects on Regiocontrol," *Synlett*, No. 20 (2007), pp. 3165-3717.
Sauthier et al., "Carbonylative 1,4-addition of potassium aryltrifluoroborates to vinyl ketones," *New J. Chem.*, vol. 33 (2009), pp. 969-971.
Selic et al., "A Simple Stereoselective One-Pot Conversion of Compounds with a Dimethylaminomethylene Group into Enol Esters," *ChemInform* vol. 31, No. 11 (2001) pp. 1743-1752.
Selvamurugan and Aidhen, "N-Methoxy-N-methyl-3-bromopropionamide: anew three carbon homologating agent for the synthesis of unsymmetrical 1,4-diketones," Tetrahedron vol. 57, No. 28 (Jul. 2001) pp. 6065-6069.
Sosnovskikh et al., "3-(Polyhaloacyl)chromones and Their Hetero Analogues: Synthesis and Reactions with Amines," Synthesis, No. 16 (2006) pp. 2707-2718.
Sosnovskikh et al., "Synthesis and some properties of 6-di(tri)fluoromethyl-and 5-di(tri)fluoroacetyl-3-methyl-1-phenylpyrano[2,3-c]pyrazol-4(1H)-ones," *Russian Chemical Bulletin*, vol. 54, No. 12 (2005), pp. 2846-2850.
Soufyane et al., "Synthesis of some fluorinatednitrogen heterocycles from (diethylaminomethylene)hexafluoroacetylacetone (DAMFA)," *Tetrahedron Letters*, vol. 34, No. 48 (Nov. 1993), pp. 7737-7740.
Voituriez et al., "Preparation of a Storable Zinc Carbenoid Species and Its Application in Cyclopropanation, Chain Extension, and [2,3]-Sigmatropic Rearrangement Reactions," *J. Org. Chem*, vol. 75, No. 4 (2010), pp. 1244-1250.
Yasuda et al., "Cross-coupling reaction of alpha-chloroketones and organotin enolates catalyzed by zinc halides for synthesis of gamma-diketones," *J Am Chem Soc.*, vol. 124, No. 25 (Jun. 2002), pp. 7440-7447.
Zhu and Zhang, "Synthesis and reaction of β,β-di(trifluoroacetyl) ethylenederivatives, $(CF_3CO)_2C=CR_1R_2$," *Journal of Fluorine Chemistry*, vol. 74, No. 2 (1995), pp. 167-170.
Agathocleous et al., "A directional Wnt/β-catenin-Sox2-proneural pathway regulates the transition from proliferation to differentiation in the *Xenopus* retina," *Development* 2009, 136(19), 3289-3299.
Akiri et al., "Wnt pathway aberrations including autocrine Wnt activation occur at high frequency in human non-small-cell lung carcinoma," *Oncogene* 2009, 28(21): 2163-2172.
Amit et al., "Axin-mediated CKI phosphorylation of β-catenin at Ser 45: a molecular switch for the Wnt pathway," Genes & Development 2002, 16(9): 1066-1076.
Baron and Rawadi, "Minireview: Targeting the Wnt/-Catenin Pathway to Regulate Bone Formation in the Adult Skeleton," *Endocrinology* Jun. 2007, 148(6): 2635-2643.
Bienz et al., "Linking Colorectal Cancer to Wnt Signaling," *Cell* 2000, 103(2): 311-320.
Bodine et al., "A small molecule inhibitor of the Wnt antagonist secreted frizzled-related protein-1 stimulates bone formation," *Bone* 2009, 44(6): 1063-1068.
Bylund et al., "Vertebrate neurogenesis is counteracted by Sox1-3 activity," *Nature Neuroscience* 2003, 6(11): 1162-1168.
Cairo et al., "Hepatic stem-like phenotype and interplay of Wnt/beta-catenin and Myc signaling in aggressive childhood liver cancer." *Cancer Cell* Dec. 2008, 14(6): 471-484.
Chen and Alman, "Wnt Pathway, an Essential Role in Bone Regeneration," 2009, *Journal of Cellular Biochemistry* 106:353-362.
Chilosi et al., "Aberrant Wnt/β-Catenin Pathway Activation in Idiopathic Pylmonary Fibrosis," *American Journal of* Pathology, 2003, 162(5): 1495-1502.
Clarke, A. R. "Wnt signalling in the mouse intestine," *Oncogene* 2006, 25(57): 7512-7521.
Corr, "Wnt—β-catenin signaling in the pathogenesis of osteoarthritis" *Nature Clinical Practice*, Oct. 2008, 4(10): 550-556.
Denayer et al., "Canonical Wnt signaling controls proliferation of retinal stem/progenitor cells in postembryonic *Xenopus* eyes," *Stem Cells* 2008, 26(8): 2063-2074.
Gerbino, *Remington: The Science and Practice of Pharmacy*, 21st Edition. Philadelphia, PA: Lippincott Williams & Wilkins, 2005.
Glass et al., "Canonical Wnt Signaling in Differentiated Osteoblasts Controls Osteoclast Differentiation," *Developmental Cell* 2005, 8(5): 751-764.
Graham et al., "SOX2 Functions to Maintain Neural Progenitor Identity," *Neuron* 2003, 39(5): 749-765.
Harris, "Cellular diversification in the vertebrate retina," *Current Opinion in Genetics& Development* 1997, 7(5): 651-658.
Huntzicker et al., "Controlling Hair Follicle Signaling Pathways through Polyubiquitination," *Investigative Dermatology* 2008, 128(5): 1081-1087.
Inestrosa and Arenas, "Emerging roles of Wnts in the adult nervous system" *Nature Reviews* 2010, 11: 77-86.
Jaenisch et al., "Stem Cells, the Molecular Circuitry of Pluripotency and Nuclear Reprogramming," *Cell* 2008, 132(4): 567-582.
Jiang et al., "Pluripotency of mesenchymal stem cells derived from adult marrow," *Nature* 2002, 418(6893): 41-49.
Kel'in and Kulinkovich, "A New Simple Synthesis of Aryl-Substituted 1,4-Diketones," *Synthesis* 1996, pp. 330-332.
Koenekoop et al., "Novel RPGR mutations with distinct retinitis pigmentosa phenotypes in French-canadian families," *American Journal of* Ophthalmology, 2003, 136(4): 678-68.
Kubo et al., "Wnt2b controls retinal cell differentiation at the ciliary marginal zone," *Development* 2003, 130(3): 587-598.
Kubo et al., "Wnt2b inhibits differentiation of retinal progenitor cells in the absence of Notch activity by downregulating the expression of proneural genes," *Development* 2005, 132(12): 2759-2770.
Lee et al., "Canonical Wnt signaling through Lef1 is required for hypothalamic neurogenesis," *Development* 2006, 133(22): 4451-4461.
Lie et al., "Wnt signalling regulates adult hippocampal neurogenesis," *Nature* 2005, 437(7063): 1370-1375.
Lindsley et al., "Canonical Wnt signaling is required for development of embryonic stem cell-derived mesoderm," *Development*, 2006, 133(19): 3787-3796.
Livesey and Cepko, "Vertebrate Neural Cell-Fate Determination: Lessons from the Retina," *Nature Reviews Neuroscience* 2001, 2: 109-118.
Logan et al., "The Wnt Signaling Pathway in Development and Diseas," *Annual Review of Cell and Developmental Biology* 2004, 20: 781-810.
Mao et al., "Low-Density Lipoprotein Receptor-Related Protein-5 Binds to Axin and Regulates the Canonical Wnt Signaling Pathway," *Molecular Cell* 2001, 7(4): 801-809.
Marson et al., "Wnt Signaling Promotes Reprogramming of Somatic Cells to Pluripotency," *Cell Stem Cell* 2008, 3(2): 132-135.

(56) References Cited

OTHER PUBLICATIONS

Marvin et al., "Inhibition of Wnt activity induces heart formation from posterior mesoderm," *Genes & Development* 2001, 15(3): 316-327.
McCrea et al., "A homolog of the armadillo protein in Drosophila (plakoglobin) associated with E-cadherin," *Science*, 1991, 254(5036): 1359-1361.
Merrill, "Develop-WNTs in Somatic Cell Reprogramming," *Cell Stem Cell* 2008, 3(5): 465-466.
Michaelidis et al., "Wnt signaling and neural stem cells: caught in the Wnt web," *Cell and Tissue Research*, 2008, 331(1): 193-210.
Moon et al., "The Promise and Perils of Wnt Signaling Through β-Catenin," *Science*, 2002, 296(5573): 1644-1646.
Morin, "Beta-catenin signaling and cancer," *BioEssays*, Dec. 1999, 21(12): 1021-1030.
Morrison, Sean J. "Neuronal potential and lineage determination by neural stem cells," *Current Opinion in Cell Biology*, 2001, 13: 666-672.
Morvan et al., "Deletion of a single allele of the Dkk1 gene leads to an increase in bone formation and bone mass ," *Journal of Bone and Mineral Research*, 2009, 21(6): 934-945.
Naito et al., "Developmental stage-specific biphasic roles of Wnt/β-catenin signaling in cardiomyogenesis and hematopoiesis," *Proc Natl Acad Sci USA*. 2006, 103(52): 19812-19817.
Okita et al., "Generation of germline-competent induced pluripotent stem cells," *Nature* (2007), 448(7151): 313-317.
Osakada et al., "Wnt Signaling Promotes Regeneration in the Retina of Adult Mammals," *Journal of Neuroscience* (2007), 27(15): 4210-4219.
Pelletier et al., "(1-(4-(Naphthalen-2-yl)pyrimidin-2-yl)piperidin-4-yl)methanamine: a wingless beta-catenin agonist that increases bone formation rate," *Journal of Medicinal Chemistry*, 2009, 52(22): 6962-6965.
Polakis, "Wnt signaling and cancer," *Genes Dev.*, 2000, 14(15): 1837-1851.
Robinson et al., "Wnt/-Catenin Signaling is a Normal Physiological Response to Mechanical Loading in Bone," *The Journal of Biological Chemistry*, Oct. 2006, 281(42): 31720-31728.
Sakanaka et al., "Casein kinase I∈ in the Wnt pathway: Regulation of β-catenin function," *Proceedings of the National Academy of Sciences of the USA* 1999, 96(22): 12548-12552.
Sampath, et al., "Isolation of osteogenin, an extracellular matrix-associated, bone-inductive protein, by heparin affinity chromatography," *Proc. Natl. Acad. Sci. USA* 1987, 84(20): 7109-7113.
Santini et al., "New molecular targets in bone metastases" *Cancer Treatment Reviews*, 36S3 (2010) S6-S10.
Schneider et al., "Wnt antagonism initiates cardiogenesis in *Xenopus laevis*," *Gene & Development*, 2001, 15(3): 304-315.
Silkstone et al., "β-Catenin in the race to fracture repair: in it to Wnt," *Nature Clinical Practice*, Aug. 2008, 4(8): 413-419.
Sperling, L. C.; "Hair anatomy for the clinician," *J. Amer. Acad. Dermatology* 1991, 25(1, Part 1): 1-17.
Tamura et al., "Role of the Wnt signaling pathway in bone and tooth," *Frontiers in Bioscience*, Jun. 2010, E2, 1405-1413.
Tashiro, et al., "A Synthetic Peptide Containing the IKVAV Sequence from the A Chain of Laminin Mediates Cell Attachment, Migration, and Neurite Outgrowth,"*The Journal of Biological Chemistry* 1989, 264(27): 16174-16182.
Tencer, et al., "The effect of local controlled release of sodium fluoride on the stimulation of bone growth," *Journal of Biomedical Materials Research* 1989, 23(6): 571-589.
Trivedi et al., "Investigational anabolic therapies for osteoporosis" *Expert Opin. Investig. Drugs*, 2010, 19(8): 995-1005.
Van Raay et al., "Frizzled 5 signaling governs the neural potential of progenitors in the developing *Xenopus* retina," *Neuron* 2005, 46(1): 23-36.
Wagner et al., "The Therapeutic Potential of the Wnt Signaling Pathway in Bone Disorders" *Current Molecular Pharmacology*, 2011, 4:14-25.
Wagner et al., "The Therapeutic Potential of the Wnt Signaling Pathway in Bone Disorders," *Current Molecular Pharmacology*, 2011, 4:14-25.
Wernig et al., "Neurons derived from reprogrammed fibroblasts functionally integrate into the fetal brain and improve symptoms of rats with Parkinson's disease," *Proc. Natl. Acad. Sci. USA* 2008, 105(15): 5856-5861.
Wong et al., "Effects of Forced Expression of an $NH_2$-terminal Truncated β-Catenin on Mouse Intestinal Epithelial Homeostasis," *The Journal of Cell Biology* 1998, 141(3): 765-777.
Wong et al., "Selection of Multipotent Stem Cells during Morphogenesis of Small Intestinal Crypts of Lieberkühn is Perturbed by Stimulation of Lef-1/β-Catenin Signaling," *The Journal of Biological Chemistry* 2002, 277(18): 15843-15850.
Xue et al., "Zinc-mediated chain extension reaction of 1,3-diketones to 1,4-diketones and diastereoselective synthesis of trans-1,2-disubstituted cyclopropanols," *Journal of Organic Chemistry* 2006, 71(1): 215-218.
Yamaguchi et al., "Histone deacetylase 1 regulates retinal neurogenesis in zebrafish by suppressing Wnt and Notch signaling pathways," *Development* 2005, 132(13): 3027-3043.
Yavropoulou and Yovos, "The role of the wnt signaling pathway in osteoblast commitment and differentiation" *Hormones*, 2007, 6(4):279-294.
Authorized Officer L. Young International Search Report and Written Opinion for PCT/US2011/48086 mailed Jan. 5, 2012, 7 pages.
Fernández-Martos et al., "Differential expression of Wnts after spinal cord contusion injury in adult rats," *PLoS One*, 6(11):e27000, 12 pages, Epub Nov. 2011.
Hollis and Zou, "Expression of the Wnt signaling system in central nervous system axon guidance and regeneration," *Front Mol Neurosci.*, 5:5, 5 pages, Feb. 2012.
Hollis and Zou, "Reinduced Wnt signaling limits regenerative potential of sensory axons in the spinal cord following conditioning lesion," *Proc Natl Acad Sci USA.*, 109(36):14663-14668, Aug. 2012.
Suh et al., "Axonal regeneration effects of Wnt3a-secreting fibroblast transplantation in spinal cord-injured rats," *Acta Neurochir (Wien)*, 153(5):1003-1010, Epub Jan. 2011.
International Preliminary Report on Patentability for PCT/US2011/48086 mailed Feb. 28, 2013, 7 pages.
Sorsak et al., "The synthesis of ethyl 2-[(2,2-dibenzoyl)ethenyl]amino-3-dimethyl-aminopropenoate and its application to the synthesis of fused 3-aminopyran-2-ones and 3-aminoazolo- and-azinopyrimidin-4(4H)-ones," *J. Heterocyclic Chem*, vol. 35, No. 6, pp. 1275-1279, Nov.-Dec. 1998.

* cited by examiner

β- AND γ-DIKETONES AND γ-HYDROXYKETONES AS WNT/β-CATENIN SIGNALING PATHWAY ACTIVATORS

RELATED APPLICATIONS

This application claims the benefit of U.S. Provisional Application No. 61/374,687, filed Aug. 18, 2010 and U.S. Provisional Application No. 61/427,974, filed Dec. 29, 2010, which are incorporated herein by reference in their entirety.

BACKGROUND OF THE INVENTION

1. Field of the Invention

This invention relates to activators of one or more proteins in the Wnt pathway, including activators of one or more Wnt proteins, and compositions comprising the same. More particularly, it concerns the use of a β-diketone, γ-diketone or γ-hydroxyketone or salts or analogs thereof, in the treatment of osteoporosis and osteoarthropathy; osteogenesis imperfecta, bone defects, bone fractures, periodontal disease, otosclerosis, wound healing, craniofacial defects, oncolytic bone disease, traumatic brain injuries related to the differentiation and development of the central nervous system, comprising Parkinson's disease, strokes, ischemic cerebral disease, epilepsy, Alzheimer's disease, depression, bipolar disorder, schizophrenia; eye diseases such as age related macular degeneration, diabetic macular edema or retinitis pigmentosa and diseases related to differentiation and growth of stem cell, comprising hair loss, hematopoiesis related diseases and tissue regeneration related diseases.

2. Description of the Related Art

The Wnt/β-catenin signaling pathway is essential in many biological processes. It regulates the fate of as-yet undeveloped cells in embryo form. The Wnt/β-catenin signaling pathway is essential to stem cell self-renewal and proliferation as well as the development of stem cells in adult organisms (e.g. skin cell, bone cell, liver cell, etc.) [*Science* (2002), 296 (5573), 1644-1646]. The Wnt/β-catenin signaling pathway regulates development, morphology, proliferation, motility and cell fate [*Annual Review of Cell and Developmental Biology* (2004), 20, 781-810]. The Wnt/β-catenin signaling pathway has a central role in tumorigenesis and inappropriate activation of this system is observed in several human cancers ["Wnt Signaling in Human Cancer", in *Signal Transduction in Cancer* (pp. 169-187). (2006) Springer]. Wnt/β-catenin was first described in humans as a protein which interacts with the cytoplasmic domain of E-cadherin and with Wnt/β-catenin, anchoring the cadherin complex to the actin cytoskeleton [*Science* (1991), 254(5036), 1359-1361]. Then, an additional role for mammalian Wnt/β-catenin was discovered; namely, as the key mediator of Wnt/β-catenin messaging.

In the presence of a Wnt ligand, if not inhibited by secreted antagonists, the Wnt ligand binds a frizzled (Fzd)/low density lipoprotein receptor related protein (LRP) complex, activating the cytoplasmic protein dishevelled (Dsh in *Drosophila* and Dvl in vertebrates). Precisely how Dsh/Dvl is activated is not fully understood, but phosphorylation by casein kinase 1 (CK1) and casein kinase 2 (CK2) have been suggested to be partly responsible [*Proceedings of the National Academy of Sciences of the USA* (1999), 96(22), 12548-12552]. Dsh/Dvl then inhibits the activity of the multiprotein complex (β-catenin-Axin-adenomatous polyposis coli (APC)-glycogen synthase kinase (GSK)-3β), which targets β-catenin by phosphorylation for degradation by the proteasome. Dsh/Dvl is suggested to bind CK1 and thereby inhibiting priming of β-catenin and indirectly preventing GSK-3β phosphorylation of β-catenin [*Genes & Development* (2002), 16(9), 1066-1076]. Upon Wnt stimulation, Dvl has also been shown to recruit GSK-3 binding protein (GBP) to the multiprotein complex. GBP might titrate GSK-3β from Axin and in this way inhibits phosphorylation of β-catenin. Finally, sequestration of Axin at the cell membrane by LRP has been described [*Molecular cell* (2001), 7(4), 801-809]. The overall result is accumulation of cytosolic β-catenin. Stabilized β-catenin will then translocate into the nucleus and bind to members of the T-cell factor (Tcf)/Lymphoid enhancing factor (Lef) family of DNA binding proteins leading to transcription of Wnt target genes.

In the absence of a Wnt ligand, Axin recruits CK1 to the multiprotein complex causing priming of β-catenin and initiation of the β-catenin phosphorylation cascade performed by GSK-3β. Phosphorylated β-catenin is then recognized by β-transducin repeat-containing protein (β-TrCP) and degraded by the proteasome, reducing the level of cytosolic β-catenin.

Aberrant activation of the Wnt/β-catenin pathway has led to several phenotypes, including the development of a variety of human cancers, and diseases leading to abnormal development and functioning of the stem cells [*Oncogene* (2009), 28(21), 2163-2172; *Cancer Cell* (2008), 14(6), 471-484; *American Journal of Pathology* (2003), 162(5), 1495-1502]. Chronic activation of the Wnt/β-catenin signaling pathway has been implicated in the development of a variety of human malignancies, including high bone mass syndrome, sclerosteosis, colorectal carcinomas, hepatocellular carcinomas (HCCs), ovarian, uterine, pancreatic carcinomas, and melanomas [*BioEssays* (1999) 21(12), 1021-1030; *Cell* (2000), 103(2), 311-320; *Genes Dev.* (2000), 14(15), 1837-1851]. Since the Wnt/β-catenin pathway is involved in myriad growth and development processes, mutation of the proteins involved in the Wnt/β-catenin signal transduction system is closely correlated with various human diseases such as abnormalities in development, hair follicle morphogenesis, stem cell differentiation, bone formation and cell proliferation.

Hair Loss

Hair forms in a pouch-like structure below the skin called a hair follicle. Visible hair, for example that seen on a human scalp, is actually the hair shaft, which is keratinized, hardened tissue that grows from the hair follicle. In particular, the hair shaft is composed largely of keratin, which is produced by keratinocytes.

Normal hair follicles cycle between a growth stage (anagen), a degenerative stage (catagen), and a resting stage (telogen). Scalp hairs have a relatively long life cycle: the anagen stage ranges from 2 to 6 years, the catagen stage ranges from a few days to a few weeks, and the telogen stage is approximately three months. Shorter hairs found elsewhere on the human body have corresponding shorter anagen durations. The morphology of the hair and the hair follicle change dramatically over the course of the life cycle of the hair [Dermatology in General Medicine (Vol. I), McGraw-Hill, Inc., 1993, pp. 290-91; Sperling, L. C.; *J. Amer. Acad. Dermatology* (1991), 25 (1, Part 1), 1-17].

During anagen, the hair follicle is highly active metabolically. The follicle comprises a dermal papilla at the base of the follicle; and epidermal matrix cells surrounding the dermal papilla form the base of the hair shaft, which extends upwards from the papilla through the hair canal. The matrix cells are the actively growing portion of the hair.

At catagen, the matrix cells retract from the papilla, and other degenerative changes occur. For example, the vessels and capillaries supplying blood and nutrients to the hair follicle shrivel and stop functioning. A column of epithelial cells pushes the keratinized proximal shaft of the hair upwards, and cell death occurs within the follicle. The hair shaft is then shed from the scalp or other part of the body and the hair follicle enters telogen, the resting stage of the hair growth cycle.

Although hair follicle regulation and growth are not well understood, they represent dynamic processes of proliferation, differentiation, and cellular interactions during tissue morphogenesis. It is believed that hair follicles are formed only in the early stages of development and are not replaced. Thus, an increase in damaged or non-functioning hair follicles is generally associated with hair loss.

Male or female pattern baldness requires the presence of male or female hormones, e.g. androgens, but the cause is unknown. The extent of hair loss in any male greatly depends on the genes he inherits from his father, mother, or both. Hair loss begins at the temples or at the top of the head. If male pattern hair loss begins in the mid-teens, subsequent hair loss is usually fairly extensive. Male balding goes in waves. Hair loss may begin in the early 20's, then stop, only to start again in a few years. By the age of 20 to 30 years, 30% of men have bald spots. This continues to rise until age 50-60, when 50% of men are completely bald.

The rate of hair loss is affected by advancing age, the tendency to bald early due to inherited genes, and an overabundance of the male hormone dihydrotestosterone (DHT) within the hair follicle. DHT acts on a hormone receptor within the hair follicle, and thereby slows hair production and produces weak, shorter hair. Sometimes DHT production even stops hair growth completely. Although balding men have above average amounts of DHT in their hair follicles, they usually do not have above average circulating testosterone levels.

Female pattern baldness is not as common as male pattern baldness, but is on the rise. It is confined to the hair predominantly at the top of the head and complete baldness is rare in females.

Toxic alopecia is temporary but typically lasts three to four months, and often is caused by an infectious disease. For example, toxic alopecia may occur as a result of hypothyroidism, diabetes, hormonal problems, vitamin deficiencies, hypopituitarism, parasites, poor digestion, early stage of syphilis, vitamin A or retinoid overdoses, or other cytotoxic drugs.

Alopecia areata is a sudden hair loss in demarcated areas. It can affect any hairy area, but most frequently affects the scalp and beard. Hair loss confined to a few areas is often reversed in a few months even without treatment but recurrence is a possibility. Alopecia areata usually occurs in people with no obvious skin disease or systemic disease, but in rare cases lab tests may show anti-microsomal antibodies to thyroglobulin, gastric parietal cells and adrenal cells.

Scarring alopecia results from inflammation and tissue destruction. It may be due to injuries such as burns, physical trauma, or destruction after x-rays. In these cases, little regrowth is expected. Other causes are cutaneous lupus erythematosus, lichen planus, chronic deep bacterial or fungal infections, deep ulcers, sarcoidosis, syphilis, or tuberculosis. Slow growing tumors of the scalp are a rare cause of hair loss.

While none of these conditions is very well understood, each condition is distressing because hair is often considered an important factor in human social communications and interactions.

Numerous approaches have been suggested for treating hair loss. Two of the most commonly used and accepted compounds for preventing hair loss are minoxidil, the active ingredient in Rogaine® and the 5α-reductase inhibitor, finasteride, the active ingredient in Propecia®. However, cosmetic treatment of age-related hair loss in patients with topical solution of minoxidil or finasteride has resulted in only moderate regrowth of hair in less than 40% of such patients. Indeed, less than ten percent of the men who use Rogaine® achieve satisfactory results. Thus, there is a need in the art for more effective methods of, and compositions for treating hair loss. Preferably, new methods and compositions will require fewer applications of active ingredients; provide hair regrowth sooner, in more abundance, and thicker, than presently observed with minoxidil or finasteride treatment.

It has been found that hair follicle development and regeneration are regulated by the canonical Wnt/β-catenin signaling pathway [*Investigative Dermatology* (2008), 128(5), 1081-1087]. In the epidermis, hair follicle development is initiated when mesenchymal cells populate the skin. During this process, signals emanating from the dermis induce epithelium thickening, elongation of the epithelial cells, and the formation of placodes containing Wnt-responsive cells. In response, placodes signal dermal cells to condense, thereby forming the dermal papilla component of the hair follicle, which is also responsive to Wnt signaling. Wnt3a is secreted from hair epithelium and acts in an autocrine and paracrine fashion, and it has been demonstrated that Wnt-3a maintains anagen gene expression in dermal papilla cells and mediates hair-inductive activity in an organ culture. This Wnt-3a-mediated hair growth might depend on the canonical Wnt/13-catenin signaling pathway because deletion of β-catenin or the Lef1 gene resulted in hair loss in mice. Therefore, activation of β-catenin by Wnt contributes to the inhibition of keratinocytes differentiation, induction of hair follicle formation, and maintenance of proliferation of neuronal progenitors.

Neurodegenerative Diseases

Neurodegenerative diseases result from deterioration of neurons or their myelin sheath which over time will lead to dysfunction and disabilities resulting from this. Adult mammalian brain has limited capacity for regeneration. This makes the repair of any injuries hazardous and, consequently, CNS traumas are devastating.

New neurons are generated from neural stem cells, in two regions of the adult mammalian central nervous system: the subventricular zone of the lateral ventricle, and the subgranular zone of the hippocampal dentate gyms [*Current Opinion in Cell Biology* (2001), 13, 666-672]. Signals provided by the microenvironment contribute to the regulation of the maintenance, proliferation and neuronal fate commitment of the local stem cells. Many of these signals and signaling pathways are unknown.

Alzheimer's disease (AD) is the most common cause of dementia that gradually destroys neurons and affects more than 24 million people worldwide. It occurs mostly in older adults and patients afflicted with AD lose their ability to learn, remember, make decisions, communicate and carry out daily activities. The etiology and progression of AD is not well understood, but is associated with amyloid beta (Aβ) plaques and neurofibrillary tangles in the brain.

Parkinson's disease (PD) is a degenerative disorder of the central nervous system affecting more than 6 million people worldwide and that often impairs the sufferer's motor skills and speech. The symptoms of Parkinson's disease result from the loss of dopamine-secreting cells in the region of the substantia nigra (literally "black substance"). These neurons project to the striatum and their loss leads to alterations in the activity of the neural circuits within the basal ganglia that regulate movement.

Amyotrophic Lateral Sclerosis (ALS) is a fatal neurodegenerative disease that results from the death of motor neurons. A progressive loss of muscle control impairs the individual's capacity for independent function. ALS strikes the cells in the brain and spinal cord (motor neurons), which send signals to move muscles. In some cases, a mutation in the SOD1 gene results in a dysfunctional protein, the superoxide dismutase protein (called SOD1), which normally "cleans" up toxic particles inside a cell. When SOD1 is mutated, toxic particles accumulate inside motor neurons causing them to malfunction. But this mutation only explains a few percent of cases of ALS. The primary cause of ALS, which afflicts about 350,000 adults worldwide, is unknown.

Stroke and traumatic brain injury can also cause neuronal loss and lead to cognitive decline. Stroke can be classified into two major categories: ischemic and hemorrhagic. Ischemia is due to interruption of the blood supply, while hemorrhage is due to rupture of a blood vessel or an abnormal vascular structure. Stroke can cause permanent neurological damage, complications and death if not promptly diagnosed and treated. It is the third leading cause of death and the leading cause of adult disability in the United States and Europe.

Frontotemporal Dementia (FTD) accounts for 18% of dementias in people under 65 years old. It frequently manifests itself as a behavioral disturbance, and can progress to impair an individual's capacity for independent thought and function. Recent studies have uncovered genetic factors that contribute to this dementia; however no treatment yet exists to block the brain deterioration it causes.

Wnt/β-catenin signal transduction system plays a crucial role in the differentiation and development of nerve cells for the central nervous system, suggesting a relationship between Wnt/β-catenin proteins and the incidence of various diseases of the central nervous system, including neurodegenerative diseases [*Nature* (2005), 437(7063), 1370-1375]. Particularly, it is also found that Wnt/β-catenin signaling is related to diseases resulting from the abnormality of nerve cells, such as brain damage, Parkinson's disease, Amyotrophic Lateral Sclerosis (Lou Gehrig's disease), stroke, epilepsy, Alzheimer's disease (AD), depression, bipolar disorder, and schizophrenia.

Alzheimer's disease is the most common age-related neurodegenerative disorder. In fact, a relationship between amyloid-β-peptide (Aβ)-induced neurotoxicity and a decrease in the cytoplasmic levels of β-catenin has been observed. Apparently Aβ binds to the extracellular cysteine-rich domain of the Frizzled receptor (Fz) inhibiting Wnt/β-catenin signaling. Cross-talk with other signaling cascades that regulate Wnt/β-catenin signaling, including the activation of M1 muscarinic receptor and PKC, the use of Ibuprofen-ChE bi-functional compounds, PPAR α, γ agonists, nicotine and some antioxidants, results in neuroprotection against Aβ. These studies indicate that a sustained loss of Wnt signaling function may be involved in the Aβ-dependent neurodegeneration observed in Alzheimer's brain. Thus, the activation of the Wnt/β-catenin signaling pathway could be proposed as a therapeutic target for the treatment of AD.

Eye Diseases

Age related macular degeneration (AMD) is a medical condition which usually affects older adults that results in a loss of vision in the center of the visual field (the macula) because of damage to the retina. It occurs in "dry" and "wet" forms. It is a major cause of visual impairment in older adults (>50 years). The inner layer of the eye is the retina, which contains nerves that communicate sight, and behind the retina is the choroid, which contains the blood supply to the macula (the central part of the retina). In the dry (nonexudative) form, cellular debris called drusen accumulate between the retina and the choroid, and the retina can become detached. In the wet (exudative) form, which is more severe, blood vessels grow up from the choroid behind the retina, and the retina can also become detached. It can be treated with laser coagulation, and with medication that stops and sometimes reverses the growth of blood vessels.

Diabetic retinopathy is retinopathy (damage to the retina) caused by complications of diabetes mellitus, which can eventually lead to blindness. It is an ocular manifestation of systemic disease which affects up to 80% of all patients who have had diabetes for 10 years or more. As new blood vessels form at the back of the eye as a part of proliferative diabetic retinopathy (PDR), they can bleed (hemorrhage) and blur vision. Some people develop a condition called macular edema. It occurs when the damaged blood vessels leak fluid and lipids onto the macula, the part of the retina that lets us see detail. As the disease progresses, severe nonproliferative diabetic retinopathy enters an advanced, or proliferative, stage. The lack of oxygen in the retina causes fragile, new, blood vessels to grow along the retina and in the clear, gel-like vitreous humour that fills the inside of the eye. Without timely treatment, these new blood vessels can bleed, cloud vision, and destroy the retina.

Retinitis pigmentosa (RP) is a group of genetic eye conditions. In the progression of symptoms for RP, night blindness generally precedes tunnel vision by years or even decades. Many people with RP do not become legally blind until their 40s or 50s and retain some sight all their lives [*American Journal of Ophthalmology* (2003), 136(4), 678-68]. Others go completely blind from RP, in some cases as early as childhood. Progression of RP is different in each case. RP is a type of progressive retinal dystrophy, a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by reduction of the peripheral visual field (known as tunnel vision) and, sometimes, loss of central vision late in the course of the disease.

Müller glia, or Müller cells, are glial cells found in the vertebrate retina, which normally serve the functions of any normal glial cells. However, following injury to the retina, it has been seen that Müller glia undergo dedifferentiation into multipotent progenitor cells. At this point, the progenitor cell can divide and differentiate into a number of retinal cell types, including photoreceptors, that may have been damaged during injury. Additionally, recently published research has shown that Müller cells act as a light collector in the mammalian eye, analogous to a fiber optic plate, funneling light to the rod and cone cells.

Multipotent retinal progenitors must solve two fundamental problems. First, they must initially expand their numbers but later limit their proliferation so that the right number of differentiated cells is produced at the appropriate developmental time. Second, the distinct processes of division and differentiation must be coordinated so that differentiation can be initiated when cells stop dividing [*Current Opinion in Genetics & Development* (1997), 7(5), 651-658; *Nature Reviews Neuroscience* (2001), (2), 109-118]. Wnt promotes cell proliferation in multiple tissues [*Cell and Tissue Research* (2008), 331(1), 193-210], in particular in the developing retina [*Stem Cells* (2008), 26(8), 2063-2074; *Development* (2003), 130(3), 587-598; *Development* (2005), 132(12), 2759-2770; *Development* (2005), 132(13), 3027-3043]. The SoxB1 family of genes (Sox1-3) may be key effectors of Wnt/β-catenin signaling in the developing nervous system

[*Development* (2006), 133(22), 4451-4461; *Neuron* (2005), 46(1), 23-36]. During neurogenesis, Sox2 antagonizes proneural genes and can maintain progenitors [*Nature Neuroscience* (2003), (6), 1162-1168; *Neuron* (2003), 39(5), 749-765]. In the frog retina, Wnt/β-catenin signaling through Fz5 is necessary for Sox2 expression, which is required for proneural gene expression and the transition from progenitors to neurons [*Neuron* (2005), 46(1), 23-36]. It was discovered that these factors are core components of a conserved hierarchical cascade and propose that they form a powerful directional network that drives cells from a proliferative, undifferentiated state to a nonproliferative, differentiated neuronal or glial fate [*Development* (2009), 136(19), 3289-3299].

Regeneration in the mammalian CNS is severely limited. Unlike in the chick, current models hold that retinal neurons are never regenerated. It has been demonstrated that, in the adult mammalian retina, Müller glia dedifferentiate and produce retinal cells, including photoreceptors, after acute neurotoxic injury in vivo. However, the number of newly generated retinal neurons is very limited. It has been demonstrated that Wnt/β-catenin signaling promotes proliferation of Müller glia-derived retinal progenitors and neural regeneration after damage or during degeneration. Wnt3a treatment increases proliferation of dedifferentiated Müller glia>20-fold in the photoreceptor-damaged retina. It has also been shown that in the degenerating retina, Wnt3a increased cell proliferation, and treatment with RA or VPA promoted the differentiation of these cells into rhodopsin-positive photoreceptor cells [*Journal of Neuroscience* (2007), 27(15), 4210-4219].

Therefore, we propose that modulating the Wnt/β-catenin pathway is one possible therapeutic strategy to enhance replacement of lost neurons by generating cells derived from endogenous neuronal progenitors.

Bone Formation

Canonical Wnt/β-catenin signaling has been demonstrated to increase bone formation, and Wnt pathway components are being pursued as potential drug targets for osteoporosis and other metabolic bone diseases [*Bone* (2009), 44(6), 1063-1068]. In modern times, bone diseases are increasing due to socio-environmental and genetic factors, particularly due to increase of population of elderly persons. Generally, bone diseases occur and develop without special symptoms, and rapidly worsen with age. Although many drugs have been developed for the treatment of bone diseases thus far, most of them mainly aim to alleviate pain or to retard the decrease of bone density. They are not effective as a curative medication which aims for increasing the bone density of patients who suffer from osteoporosis. Some other drugs are usually in the form of injections and are reported to produce side effects upon long-term administration thereof.

Signaling through the Wnt/β-catenin pathway can increase bone mass through a number of mechanisms, including renewal of stem cells, stimulation of preosteoblast replication, induction of osteoblastogenesis, and inhibition of osteoblast and osteocyte apoptosis. One molecular mechanism is through the stimulation of the Wnt pathway by Wnt-3a interaction of its receptors LRP5 and Fzd [*Journal of Medicinal Chemistry* (2009), 52(22), 6962-6965]. Bone forming osteoblasts express the proteins LRP5 and Fzd on the surface membrane, which serve as co-receptors for the soluble peptide agonist Wnt-3a. Once stimulated with Wnt-3a, internal concentrations of free β-catenin rise and enter the nucleus and recruit T-cell factor (TCF). Transcriptional events follow and result in the production of additional anabolic gene products. An additional soluble extracellular protein, Dkk-1, antagonizes this process by simultaneously binding to the cell surface receptors Kr2 and LRP5, effectively inhibiting Wnt-3a binding to LRP5. In addition, the Kr2/LRP5/Dkk-1 complex undergoes endocytosis to remove LRP5 from the cell membrane, thereby nullifying its function. Loss-of-function mutations of secreted Wnt antagonists like Dkk-1, SOST/sclerostin and secreted frizzled-related protein (sFRP)-1 result in increased bone formation due to changes in a variety of osteoblast parameters like proliferation, differentiation, recruitment/longevity and function [*Journal of Bone and Mineral Research* (2009), 21(6), 934-945], while deletion of the β-catenin-activated transcription factor TCF-1 causes osteopenia that arises from a reduction in osteoprotegerin expression by the osteoblast [*Developmental Cell* (2005), 8(5), 751-764].

Intestinal Diseases

The adult intestinal epithelium is characterized by continuous replacement of epithelial cells through a stereotyped cycle of cell division, differentiation, migration and exfoliation occurring during a 5-7 day crypt/villus transit time. The putative growth factors regulating proliferation within the adult intestinal stem cell niche have not yet been identified, although studies have implicated the cell-intrinsic action of β-catenin/Lef/Tcf signaling within the proliferative crypt compartment.

A number of pathological conditions affect the cells of the intestines. Inflammatory bowel disease (IBD) can involve either or both the small and large bowel. Crohn's disease and ulcerative colitis are the best-known forms of IBD, and both fall into the category of "idiopathic" inflammatory bowel disease because the etiology for them is unknown. "Active" IBD is characterized by acute inflammation. "Chronic" IBD is characterized by architectural changes of crypt distortion and scarring. Crypt abscesses can occur in many forms of IBD.

Ulcerative colitis (UC) involves the colon as a diffuse mucosal disease with distal predominance. The rectum is virtually always involved, and additional portions of colon may be involved extending proximally from the rectum in a continuous pattern. The etiology for UC is unknown. Patients with prolonged UC are at increased risk for developing colon cancer.

Patients with UC are also at risk for development of liver diseases including sclerosing cholangitis and bile duct carcinoma.

Crohn's disease can involve any part of the GI tract, but most frequently involves the distal small bowel and colon. Inflammation is typically transmural and can produce anything from a small ulcer over a lymphoid follicle (aphthoid ulcer) to a deep fissuring ulcer to transmural scarring and chronic inflammation. One third of cases have granulomas, and extracolonic sites such as lymph nodes, liver, and joints may also have granulomas. The transmural inflammation leads to the development of fistulas between loops of bowel and other structures. Inflammation is typically segmental with involved bowel separating areas of involved bowel. The etiology is unknown, though infectious and immunologic mechanisms have been proposed.

Gluten, a common dietary protein present in wheat, barley and rye causes a disease called Celiac disease in sensitive individuals. Ingestion of such proteins by sensitive individuals produces flattening of the normally luxurious, rug-like, epithelial lining of the small intestine.

Other clinical symptoms of Celiac disease include fatigue, chronic diarrhea, malabsorption of nutrients, weight loss, abdominal distension, anemia, as well as-a substantially enhanced risk for the development of osteoporosis and intestinal malignancies such as lymphoma and carcinoma. Celiac disease is generally considered to be an autoimmune disease and the antibodies found in the serum of the patients support the theory that the disease is immunological in nature.

Transgenic mice that have a knock-out of the Tcf locus show a loss of proliferative stem cell compartments in the small intestine during late embryogenesis [*Oncogene* (2006) 25(57), 7512-7521]. However, the knockout is lethal, and so has not been studied in adults. In chimeric transgenic mice that allow analysis of adults, expression of constitutively active $NH_2$-truncated p-catenin stimulated proliferation in small intestine crypts, although either $NH_2$-truncated p-catenin or Lef-1/-catenin fusions induced increased crypt apoptosis as well [*The Journal of Cell Biology* (1998), 141(3), 765-777; The Journal of Biological Chemistry (2002), 277 (18), 15843-15850]. Because diverse factors regulate β-catenin/Lef/Tcf-dependent transcription, including non-Frizzled GPCRs and PTEN/PI-3-kinase, the cause of intestinal stem cell defect is not known. Genes expressed in the gastrointestinal tract that are controlled by Wnt/β-catenin include CD44, and EphB2.

Regenerative Medicine

Due to the remarkable advances made in the field of medicine in recent years, opportunities for saving lives are continuing to increase in the area of living donor transplant techniques for tissues and organs. However, there are limitations on treatment dependent upon living donor transplants due to such factors as a shortage of transplant donors and the occurrence of rejection. If it were possible to regenerate a tissue or organ that has been lost due to surgical treatment or an unforeseen accident, then it would be possible to considerably improve the quality of life for patients. In addition, regenerative medicine also makes it possible to resolve the problems confronting living donor transplants. From this viewpoint, the degree of expectations being placed on regenerative medicine is high.

Technologies in which regenerative medicine has been successful are primarily related to comparatively simple tissue in terms of morphology or function in the manner of artificial skin, artificial bone and artificial teeth. Reconstructed artificial skin and artificial bone is incorporated into cells enabling the providing of signals required for tissue construction. However, there have been limitations on the repertoire of differentiation of artificial skin and artificial bone by regenerative medicine techniques. For example, although allogeneic keratinocytes or skin fibroblasts and the like differentiate into structures in the form of the epidermis, are incorporated by surrounding organs to eventually have a horny layer or basal layer having barrier properties, there has been reported to be no derivation of secondary derivatives such as hair follicles, sebaceous glands or sweat glands.

Body tissue normally contains both cells that are able to self-replicate and possess stem cell properties for maintaining tissue homeostasis by sending signals to differentiated cells or supplying differentiated cells, and cells having properties of somatic cells that have already differentiated that receive various signals or commands from such cells, and is able to function through interaction between both of these types of cells. In the case of vertebrates, for example, interaction between mesenchymal cells and epithelial cells is essential for nearly all tissue and organ formation. In the case of hair follicles, mesenchymal cells in the form of hair papilla cells are responsible for stem cell-like properties, while epithelial cells in the form of keratinocytes are equivalent to cells having somatic cell-like properties in their ability to differentiate into hair shafts (hair itself).

The difficulty encountered when forming organs by regenerative medicine lies in reaching a state of coexistence between cells having stem cell-like properties maintained in an undifferentiated state and cells that have already differentiated as in actual body tissue. In the prior art, even if epithelial cells and mesenchymal cells were able to be co-cultured, they either both ended up differentiating or both maintained an undifferentiated state, thereby preventing the reproduction of the coexistence of undifferentiated cells and differentiated cells so as to mimic actual body tissue.

Guiding multipotent cells into distinct lineages and controlling their expansion remain fundamental challenges in developmental and stem cell biol. Members of the Wnt pathway control many pivotal embryonic events, including self-renewal or expansion of progenitor cells.

Published observations suggest that canonical Wnt signals play distinct roles during discrete developmental windows, first positively regulating mesoderm commitment and then possibly playing a negative role in the initial induction of cardiac progenitors [*Genes & Development* (2001), 15(3), 316-327; Ibid., 304-315; *Proc Natl Acad Sci USA*. (2006), 103(52), 19812-19817; *Development* (Cambridge, UK) (2006), 133(19), 3787-3796]. The loss- and gain-of-function studies of canonical Wnt signaling in a spatiotemporally restricted manner described here provide compelling evidence that Wnt/β-catenin signaling is required in a cell autonomous fashion for the expansion and development of precardiac mesoderm and cardiac mesoderm in mouse. Thus, narrow developmental windows may exist during which canonical Wnt signaling sequentially inhibits then promotes cardiac development. Thus it was shown that canonical Wnt signaling can be manipulated to regulate expansion and differentiation of progenitor cells.

In contrast to progenitor cells, however, stem cells are far less specific. The most important difference between stem cells and progenitor cells is that stem cells can replicate indefinitely, whereas progenitor cells can only divide a limited number of times. The term adult stem cell, also known as somatic and gametes, refers to any cell which is found in a developed organism that has two properties: the ability to divide and create another cell like itself and also divide and create a cell more differentiated than itself. They can be found in children, as well as adults [*Nature* (2002), 418(6893), 41-49]. All somatic cells of an individual are genetically identical in principle, they evolve a variety of tissue-specific characteristics during the process of differentiation, through epigenetic and regulatory alterations. Pluripotent somatic stem cells are rare and generally small in number but can be found in a number of tissues including umbilical cord blood. A great deal of somatic stem cell research has focused on clarifying their capacity to divide or self-renew indefinitely and their differentiation potential. In mice, pluripotent stem cells are directly generated from adult fibroblast cultures. Unfortunately, many mice don't live long with stem cell organs.

Somatic cells can be reprogrammed to induced pluripotent stem cells (iPSC) by retroviral transduction of four transcription factors [*Cell* (2008), 132(4), 567-582]. While the reprogrammed pluripotent cells are thought to have great potential for regenerative medicine [*Proc. Natl. Acad. Sci. USA* (2008), 105(15), 5856-5861], genomic integrations of the retroviruses, especially c-Myc, increase the risk of tumorigenesis [*Nature* (2007), 448(7151), 313-317]. Generation of iPSCs for use in the clinical setting would benefit from identification of alternative, ultimately safer, initiating stimuli, in preference to genetic modification. This could be transient treatment with defined factors, low-toxicity chemicals, or synthetic small molecules. Since the Wnt pathway is intimately connected to the core circuitry of pluripotency, it has been shown that the stimulation of the pathway using soluble Wnt3a promotes the generation of iPSCs in the absence of c-Myc retrovirus. These data demonstrate that signal transduction pathways and transcription factors can act coordinately to reprogram differentiated cells to a pluripotent state [*Cell Stem Cell* (2008), 3(2), 132-135; Cell Stem Cell (2008), 3(5), 465-466].

As discussed above, activators of the Wnt/β-catenin signaling pathway are expected to be medicaments useful against cell proliferation disorders, bone disorders, eye diseases, Alzheimer's disease and even tissue generation. Thus, it would be advantageous to have novel activators of the Wnt/β-catenin signaling pathway as potential treatment regimens for Wnt/β-catenin signaling pathway-related disorders. The instant invention is directed to these and other important ends.

SUMMARY OF THE INVENTION

The present invention relates to a method for increasing cell or tissue regeneration in a vertebrate subject. The invention relates to methods for increasing the successful activity of embryonic and/or adult stem cells, progenitor cells, mesenchymal progenitor/stem cells and/or differentiated cells in vivo in a vertebrate subject. The invention further relates to methods for increasing cell or tissue regeneration in a vertebrate subject by administering a compound according to Formulas I, II or III, to the vertebrate subject in need thereof, and increasing in vivo a stem cell, progenitor cell, and/or differentiated cell population in the vertebrate subject compared to the stem cell, progenitor cell, and/or differentiated cell population in the vertebrate subject before treatment, to increase cell or tissue regeneration in the vertebrate subject. Increasing the stem cell, progenitor cell, or differentiated cell population in the vertebrate subject can be a result of cell proliferation, cell homing, decreased apoptosis, self-renewal, or increased cell survival.

In one embodiment, the cell or tissue regeneration can occur in tissues including but not limited to, bone, chondrocytes/cartilage, muscle, skeletal muscle, cardiac muscle, pancreatic cells, endothelial cells, vascular endothelial cells, adipose cells, liver, skin, connective tissue, hematopoietic stem cells, neonatal cells, umbilical cord blood cells, fetal liver cells, adult cells, bone marrow cells, peripheral blood cells, erythroid cells, granulocyte cells, macrophage cells, granulocyte-macrophage cells, B cells, T cells, multipotent mixed lineage colony types, embryonic stem cells, mesenchymal progenitor/stem cells, mesodermal progenitor/stem cells, neural progenitor/stem cells, or nerve cells. The vertebrate can be mammalian, avian, reptilian, amphibian, osteichthyes, or chondrichthyes.

In one embodiment, the present invention is a composition for preventing or decreasing the loss of hair and/or for stimulating or increasing hair growth or regrowth, wherein the composition comprises a compound according to Formulas I, II or III.

One embodiment of the present invention provides a pharmaceutical composition for the treatment of a neurodegenerative disease.

In another embodiments, the neurological disorder is Alzheimer's disease, schizophrenia or schizo-affective disorder, bipolar disorder or unipolar disorder, depression, substance abuse, neurodegenerative disease, autism or autism spectrum disorder, or a disorder resulting from neural damage such as spinal injuries or brain injuries. The neurodegenerative disease may be for instance, amyotrophic lateral sclerosis (Lou Gehrig's disease) or Parkinson's disease. In some embodiments, the invention provides methods for treating brain injury resulting from traumatic injury or stroke.

In another embodiments, the neurological disorder is an eye disease such as age related macular degeneration, diabetic macular edema or retinitis pigmentosa.

In one embodiment, the invention relates to a method for (i) reducing loss of bone mass or bone density, (ii) increasing bone mass or bone density, (iii) maintaining bone mass or bone density and/or (iv) reducing loss of calcium from bone, comprising: administering to a subject a therapeutically effective amount of a compound according to Formulas I, II or III. As used in this patent specification, the term "bone mass" and "bone density" are used interchangeably.

In one embodiment, the invention relates to a method to regulate osteoblast activity or osteoclast activity comprising the use of a compound according to Formulas I, II or III. Osteoblast activity can be regulated by regulating the proliferation or function of osteoblasts. The function of osteoblasts and/or osteoclasts can be regulated directly or indirectly.

In one embodiment, the method is for the treatment of a bone condition or a bone defect.

In another embodiment, the bone condition being treated is frailty, an osteoporotic fracture, a bone defect, childhood idiopathic bone loss, alveolar bone loss, mandibular bone loss, bone fracture, osteotomy, bone loss associated with periodontitis, or prosthetic ingrowth.

In yet another embodiment, the bone condition being treated is Paget's disease.

In another embodiment, the bone condition being treated is oncolytic bone disease.

In another embodiment, the invention relates to method for promoting healing of bone fractures, bone defects, craniofacial defects, otosclerosis or osteogenesis imperfecta comprising: administering to a subject a therapeutically effective amount of a compound according to Formulas I, II or III.

In another embodiment, the invention relates to method for bone tissue engineering comprising the use a compound according to Formulas I, II or III. In one embodiment the cells used for bone tissue engineering are treated with a compound according to Formulas I, II or III.

In another embodiment, the invention relates to the use of a compound according to Formulas I, II or III as a medicament for (i) reducing loss of bone mass, (ii) increasing bone mass, (iii) maintaining bone mass and/or (iv) reducing loss of calcium from bone in a subject in need thereof. In another embodiment, the invention relates to the use of a compound according to Formulas I, II or III as a medicament for healing bone fractures or repairing bone defects in a mammal.

In one embodiment, the bone condition being treated is osteoporosis. In one embodiment, the osteoporosis being treated is selected from the group consisting of: glucocorticoid-induced osteoporosis, hyperthyroidism-induced osteoporosis, immobilization-induced osteoporosis, heparin-induced osteoporosis and immunosuppressive-induced osteoporosis.

In one embodiment, a compound according to Formulas I, II or III is administered conjointly with an agent that increases bone mass or prevents the loss of bone mass. In one embodiment, the agent that increases bone mass is a growth factor, a mineral, a vitamin, a hormone, a prostaglandin, an inhibitor of 15-lipoxygenase, a bone morphogenic protein or another member of the TGF-beta superfamily which increases bone formation, an ACE inhibitor, a Hedgehog protein, examethasone, calcitonin, or an active fragment thereof. In one embodiment, the agent that prevents the loss of bone mass is progestin, estrogen, an estrogen/progestin combinations, estrone, estriol, 17α- or 17β-ethynyl estradiol, SB242784, polyphosphonates, biphosphonates or an active fragment thereof In one embodiment of the invention, a compound according to Formulas I, II or III, is administered to enhance proliferation of intestinal epithelium, for the treatment, or as a therapeutic adjunct in the treatment, of diseases that compromise the intestinal epithelia, including inflammatory bowel diseases and Celiac disease.

In another embodiment, the invention relates to a method for organ tissue engineering comprising the use of a compound according to Formulas I, II or III. In one embodiment the cells used for organ tissue engineering are treated with a compound according to Formulas I, II or III.

Some embodiments disclosed herein include a Wnt/β-catenin signaling pathway activator containing a β-diketone, γ-diketone or γ-hydroxyketone core. Other embodiments disclosed herein include pharmaceutical compositions and methods of treatment using these compounds.

One embodiment of a Wnt/β-catenin signaling pathway activator disclosed herein includes a compound having the structure of Formula I:

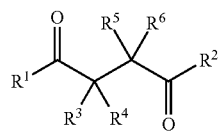

I $R^1$ is selected from the group consisting of substituted or unsubstituted heteroaryl and substituted or unsubstituted heterocyclyl, with the proviso that a carbon atom is attached to the carbonyl;

$R^2$ is selected from the group consisting of substituted or unsubstituted aryl, substituted or unsubstituted heteroaryl, substituted or unsubstituted carbocyclyl and substituted or unsubstituted heterocyclyl, with the proviso that a carbon atom is attached to the carbonyl; and $R^3$, $R^4$, $R^5$ and $R^6$ are independently selected from a group consisting of H, —$C_{1-9}$alkyl, —$C_{1-9}$alkylaryl and —$C_{1-9}$alkylheteroaryl.

Another embodiment of a Wnt/β-catenin signaling pathway activator disclosed herein includes a compound having the structure of Formula II:

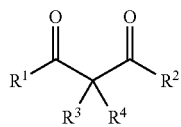

II $R^1$ is selected from the group consisting of substituted or unsubstituted heteroaryl and substituted or unsubstituted heterocyclyl, with the proviso that a carbon atom is attached to the carbonyl;

$R^2$ is selected from the group consisting of substituted or unsubstituted aryl, substituted or unsubstituted heteroaryl, substituted or unsubstituted carbocyclyl and substituted or unsubstituted heterocyclyl, with the proviso that a carbon atom is attached to the carbonyl; and $R^3$ and $R^4$ are independently selected from a group consisting of H, —$C_{1-9}$alkyl, —$C_{1-9}$alkylaryl and —$C_{1-9}$alkylheteroaryl.

Another embodiment of a Wnt/β-catenin signaling pathway activator disclosed herein includes a compound having the structure of Formula III:

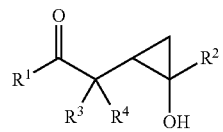

III $R^1$ is selected from the group consisting of substituted or unsubstituted aryl, substituted or unsubstituted heteroaryl, substituted or unsubstituted carbocyclyl and substituted or unsubstituted heterocyclyl, with the proviso that a carbon atom is attached to the carbonyl;

$R^2$ is selected from the group consisting of substituted or unsubstituted aryl, substituted or unsubstituted heteroaryl, substituted or unsubstituted carbocyclyl and substituted or unsubstituted heterocyclyl, with the proviso that a carbon atom is attached to the carbonyl; and $R^3$ and $R^4$ are independently selected from a group consisting of H, —$C_{1-9}$alkyl, —$C_{1-9}$alkylaryl and —$C_{1-9}$alkylheteroaryl.

Some embodiments include stereoisomers and pharmaceutically acceptable salts of a compound of Formulas I, II or III.

Some embodiments include pro-drugs of a compound of Formulas I, II and III.

Some embodiments of the present invention include pharmaceutical compositions comprising a compound of Formulas I, II or III and a pharmaceutically acceptable carrier.

Another embodiment disclosed herein includes a pharmaceutical composition comprising a compound according to any of the above formulas and a pharmaceutically acceptable carrier, diluent, or excipient.

Some embodiments of the present invention include methods to prepare compounds of Formulas I, II or III.

It is to be understood that both the foregoing general description and the following detailed description are exemplary and explanatory only and are not restrictive of the invention, as claimed.

DETAILED DESCRIPTION OF THE INVENTION

It has been discovered that β-diketones, γ-diketones and γ-hydroxyketones are capable of activating the Wnt/β-catenin signaling pathway. The Wnt/β-catenin signaling pathway has been found to play a crucial role in the differentiation and development of nerve cells for the central nervous system, bone formation, hair follicle development and regeneration, and stimulation of stem cell growth, maintenance and differentiation.

The present invention relates a method for increasing cell or tissue regeneration in a vertebrate subject. The invention relates to methods for increasing the successful activity of embryonic and/or adult stem cells, progenitor cells, mesenchymal progenitor/stem cells, or differentiated cells in vivo in a vertebrate subject. The invention further relates to methods for increasing cell or tissue regeneration in a vertebrate subject by administering a compound according to Formulas I, II or III to the vertebrate subject in need thereof, and increasing in vivo a stem cell, progenitor cell population, or differentiated cell in the vertebrate subject compared to the stem cell or progenitor cell, or differentiated cell population in the vertebrate subject before treatment, to increase cell or tissue regeneration in the vertebrate subject. A method for increasing stem cell or progenitor cell population is provided to repair or replace damaged tissue in a vertebrate subject, wherein the cell or tissue regeneration occurs in bone, chondrocytes/cartilage, muscle, skeletal muscle, cardiac muscle, pancreatic cells, endothelial cells, vascular endothelial cells, adipose cells, liver, skin, connective tissue, hematopoietic stem cells, neonatal cells, umbilical cord blood cells, fetal liver cells, adult cells, bone marrow cells, peripheral blood cells, erythroid cells, granulocyte cells, macrophage cells, granulocyte-macrophage cells, B cells, T cells, multipotent mixed lineage colony types, embryonic stem cells, mesenchymal progenitor/stem cells, mesodermal progenitor/stem cells, neural progenitor/stem cells, or nerve cells.

Hair Growth

Compositions comprising compounds according to Formulas I, II or III can be used to promote hair growth.

"Promoting hair growth" refers to maintaining, inducing, stimulating, accelerating, or revitalizing the germination of hair.

The method of the present invention is useful in the treatment of alopecia in mammals, and as such may be used to promote, increase, or assist in the growth of hair. Subjects may be male or female. The term alopecia refers to both the complete absence of hair in skin which typically exhibits hair growth, as well as to a loss or diminution in the amount of hair. Multiple types and causes of alopecia are recognized in humans, including male pattern baldness, chemotherapy induced hair loss, congenital alopecia, and alopecia areata. The term treating alopecia refers to both the treatment of skin with a total absence of hair growth as well as the treatment of skin having reduced or patchy hair growth. Successful treatment results in an increased number of hairs.

Subjects to be treated according to the invention include human subjects as well as other mammalian subjects, such as dogs, cats, mice, rats, goats, llamas, minks, seals, beavers, ermines, and sheep. These can be treated for hair loss due or simply for enhancing wool or pelt production.

"Treating alopecia" refers to (i) preventing alopecia in an animal which may be predisposed to alopecia, (ii) inhibiting, retarding or reducing alopecia, (iii) promoting hair growth and/or (iv) prolonging the anagen phase of the hair cycle.

A method for promoting hair growth in accordance with the present invention is characterized by applying an effective amount of a compound according to Formulas I, II or III, or a pharmacologically acceptable salt thereof on the skin of mammals and in particular, on human scalp.

Neurological Disorder

Compounds according to the present invention can modulate the cellular fate of neural stem cells and promote the differentiation of these neural precursors to functional neurons and glial cells.

Compositions comprising compounds according to Formulas I, II or III can be used to treat neurodegenerative diseases.

Non-limiting examples of neurodegenerative diseases are Alzheimer's disease, schizophrenia or schizo-affective disorder, bipolar disorder or unipolar disorder, depression, substance abuse, neurodegenerative disease, autism or autism spectrum disorder, or a disorder resulting from neural damage such as spinal injuries or brain injuries. The neurodegenerative disease may be for instance, amyotrophic lateral sclerosis (Lou Gehrig's disease) or Parkinson's disease.

Other non-limiting examples of neurodegenerative diseases are eye diseases such as age related macular degeneration, diabetic macular edema or retinitis pigmentosa.

The invention also provides a method for treating brain injury resulting from traumatic injury or stroke.

Another aspect of the invention is a method of enhancing neural progenitor proliferation and differentiation by contacting a neural progenitor cell with a compound according to Formulas I, II or III in an effective amount to enhance neural progenitor proliferation and differentiation.

In one aspect the invention provides a method of enhancing nerve generation, by contacting a nerve with a compound according to Formulas I, II or III in an effective amount to enhance nerve generation.

In another aspect, the present invention provides a method of treating a neurodegenerative disease in a patient requiring treatment, which comprises administering an effective amount of a compound of Formulas I, II or III, or a pharmaceutically acceptable salt thereof as defined hereinabove.

The compounds according to the present invention may be administered alone or co-administered with compounds working by a different mechanism, for example neuroprotectant agents. In one embodiment, the compounds are co-administered compounds with an acetylcholinesterase inhibitor (e.g. Aricept) for Alzheimer's disease or L-DOPA for Parkinson disease.

Bone Formation

Compositions comprising compounds of Formulas I, II or III can be used to treat, prevent and alleviate bone conditions. The present invention provides a method for (i) reducing loss of bone mass, (ii) increasing bone mass, (iii) maintaining bone mass and/or (iv) reducing loss of calcium from bone, comprising: administering to a subject a therapeutically effective amount of a compound according to Formulas I, II or III. The method could be used for treating, preventing or delaying a bone condition. The invention further provides a method for promoting healing of bone fractures or bone defects comprising: administering to a subject a therapeutically effective amount of a compound according to Formulas I, II or III. Any of the above mentioned methods can involve the conjoint administration of an agent that increases bone mass or prevents the loss of bone mass.

The invention also provides for the use of a compound according to Formulas I, II or III as a medicament for treating, preventing or delaying a bone condition.

As used herein, the term "bone condition" includes any condition where it is desirable to increase bone mass or bone density and/or prevent the loss of bone mass or bone density. A bone condition includes any condition that increases osteoclast number, increases osteoclast activity, increases bone resorption, increases marrow fibrosis, or alters the calcium content of bone.

Non-limiting examples of bone conditions include metabolic bone conditions such as renal osteodystrophy, primary forms of osteoporosis (e.g., postmenopausal and senile osteoporosis), and secondary forms of osteoporosis that develop as a result of an underlying disease state. For example, osteoporosis can develop in patients that have endocrine disorders such as hyperparathyroidism, hypo- and hyperthyroidism, hypogonadism, hypercalcemia due to malignancy, pituitary tumors, type I diabetes, or Addison's disease. Neoplasias such as multiple myeloma and carcinomatosis also can lead to development of osteoporosis. In addition, gastrointestinal problems such as malnutrition, malabsorption, hepatic insufficiency, and vitamin C or D deficiencies, and chronic administration of drugs such as anticoagulants, chemotherapeutics, corticosteroids, anticonvulsants, and alcohol can lead to development of osteoporosis.

Non-limiting examples of bone conditions also include osteonecrosis, osteoarthritis, rheumatoid arthritis, Paget's disease, osteogenesis imperfecta, chronic hyperparathyroidism, hyperthyroidism, Gorham-Stout disease, McCune-Albright syndrome, and alveolar ridge bone loss.

The term "bone condition" includes, without limitation, all conditions resulting in bone loss, including, cancers and tumors (such as osteosarcoma and multiple myeloma), renal disease (including acute renal failure, chronic renal failure, renal bone dystrophy and renal reperfusion injury), kidney disease, premature ovarian failure and other conditions.

Endocrine disorders, vitamin deficiencies and viral infections also can lead to development of bone conditions that can be treated with methods of the invention. An example of a bone condition caused by a nutritional disorder is osteomalacia, a nutritional disorder caused by a deficiency of vitamin D and calcium. It is referred to as "rickets" in children, and "osteomalacia" in adults. It is marked by a softening of the bones (due to impaired mineralization, with excess accumulation of osteoid), pain, tenderness, muscle wasting and weakness, anorexia, and overall weight loss. It can result from malnutrition, repeated pregnancies and lactation (exhausting or depleting vitamin D and calcium stores), and vitamin D resistance.

Bone conditions include conditions resulting from the treatment of a subject with drugs, for example the osteopenia resulting from the treatment with Cyclosporin A or FK506.

Bone conditions also include bone fractures, bone trauma, conditions associated with post-traumatic bone surgery, post-prosthetic joint surgery, post-plastic bone surgery, post-dental surgery, bone chemotherapy, post-dental surgery and bone radiotherapy. Fractures include all types of microscopic and macroscopic fractures. Examples of fractures includes avulsion fracture, comminuted fracture, transverse fracture, oblique fracture, spiral fracture, segmental fracture, displaced fracture, impacted fracture, greenstick fracture, torus fracture, fatigue fracture, intra-articular fracture (epiphyseal fracture), closed fracture (simple fracture), open fracture (compound fracture) and occult fracture.

Other non-limiting examples of bone conditions include bone deformation, spinal deformation, prosthesis loosening, bone dysplasia, scoliosis, periodontal disease and defects, tooth repair, and fibrous osteitis.

The invention also provides a method for treating a subject with a therapeutically effective amount of a compound according to Formulas I, II or III, wherein the subject is in need of bone repair following surgery, such as cranio-maxillofacial repair following tumor removal, surgical bone reconstruction following traumatic injury, repair of hereditary or other physical abnormalities, and promotion of bone healing in plastic surgery.

The invention also provides a method for treating a subject with a therapeutically effective amount of a compound according to Formulas I, II or III, wherein the subject is in need of bone repair after receiving an implant (including joint replacements and dental implants), a prosthesis or a bone graft.

The invention also provides a method for treating a subject with a therapeutically effective amount of a compound according to Formulas I, II or III, wherein the subject: a) is in need of increased bone density or bone healing; b) has undergone or is presently undergoing corticosteroid therapy, dialysis, chemotherapy for post-menopausal bone loss, radiation therapy for cancer or hormone replacement therapy; c) is immobilized or subjected to extended bed rest due to bone injury; d) suffers from alcoholism, diabetes, hyperprolactinemia, anorexia nervosa, primary and secondary amenorrhea, or oophorectomy; e) suffers from renal failure; f) is 50 years or older; or g) is a female.

The invention also provides a method for treating a subject with a therapeutically effective amount of a compound according to Formulas I, II or III, wherein the subject is affected by a disease selected from arterial calcification, ankylosing spondylitis, ossification of the posterior longitudinal ligament, myositis ossificans, diffuse idiopathic skeletal hyperostosis, calcific tendonitis, rotator cuff disease of the shoulders, bone spurs, cartilage or ligament degeneration due to hydroxyapatite crystal deposition, and chondrocalcinosis.

By the term "effective amount" or "therapeutically effective amount" of a compound according to Formulas I, II or III, is meant an amount sufficient to obtain the desired physiological effect, e.g., activation of osteoblasts, increase in osteoblast number, increase in bone formation, a decrease in osteoclasts number or the deactivation of osteoclasts. An effective amount of a Wnt/β-catenin signaling pathway activator is determined by the care giver in each case on the basis of factors normally considered by one skilled in the art to determine appropriate dosages, including the age, sex, and weight of the subject to be treated, the condition being treated, and the severity of the medical condition being treated.

The invention also provides a method for treating a subject with a therapeutically effective amount of a compound according to Formulas I, II or III conjointly with an agent that increases bone mass or prevents the loss of bone mass. In one embodiment, the agent that increases bone mass is a growth factor, a mineral, a vitamin, a hormone, a prostaglandin, an inhibitor of 15-lipoxygenase, a bone morphogenic protein or another member of the TGF-beta superfamily which increases bone formation, an ACE inhibitor, a Hedgehog protein, examethasone, calcitonin, or an active fragment thereof. In one embodiment, the agent that prevents the loss of bone mass is progestin, estrogen, an estrogen/progestin combinations, estrone, estriol, 17α- or 17β-ethynyl estradiol, SB242784, polyphosphonates, biphosphonates or an active fragment thereof.

Intestinal Diseases

Compounds according to Formulas I, II or III are also administered for the treatment of gastrointestinal inflammation. "Gastrointestinal inflammation" as used herein refers to inflammation of a mucosal layer of the gastrointestinal tract, and encompasses acute and chronic inflammatory conditions. Acute inflammation is generally characterized by a short time of onset and infiltration or influx of neutrophils.

"Chronic gastrointestinal inflammation" refers to inflammation of the mucosal of the gastrointestinal tract that is characterized by a relatively longer period of onset, is long-lasting (e.g., from several days, weeks, months, or years and up to the life of the subject), and is associated with infiltration or influx of mononuclear cells and can be further associated with periods of spontaneous remission and spontaneous occurrence. Thus, subjects with chronic gastrointestinal inflammation may be expected to require a long period of supervision, observation, or care. "Chronic gastrointestinal inflammatory conditions" (also referred to as "chronic gastrointestinal inflammatory diseases") having such chronic inflammation include, but are not necessarily limited to, inflammatory bowel disease (IBD), colitis induced by environmental insults (e.g., gastrointestinal inflammation (e.g., colitis) caused by or associated with (e.g., as a side effect) a therapeutic regimen, such as administration of chemotherapy, radiation therapy, and the like), colitis in conditions such as chronic granulomatous disease, celiac disease, celiac sprue (a heritable disease in which the intestinal lining is inflamed in response to the ingestion of a protein known as gluten), food allergies, gastritis, infectious gastritis or enterocolitis (e.g., *Helicobacter pylori*-infected chronic active gastritis) and other forms of gastrointestinal inflammation caused by an infectious agent, and other like conditions.

As used herein, "inflammatory bowel disease" or "IBD" refers to any of a variety of diseases characterized by inflammation of all or part of the intestines. Examples of inflammatory bowel disease include, but are not limited to, Crohn's disease and ulcerative colitis. Reference to IBD throughout the specification is often referred to in the specification as exemplary of gastrointestinal inflammatory conditions, and is not meant to be limiting.

Compounds according to Formulas I, II or III can be administered to a subject prior to onset of more severe symptoms (e.g., prior to onset of an acute inflammatory attack), or after onset of acute or chronic symptoms (e.g., after onset of an acute inflammatory attack). As such, the agents can be administered at any time, and may be administered at any interval. In one embodiment, compounds according to Formulas I, II or III are administered about 8 hours, about 12 hours, about 24 hours, about 2 days, about 4 days, about 8 days, about 16 days, about 30 days or 1 month, about 2 months, about 4 months, about 8 months, or about 1 year after initial onset of gastrointestinal inflammation-associated symptoms and/or after diagnosis of gastrointestinal inflammation in the subject.

When multiple doses are administered, subsequent doses are administered within about 16 weeks, about 12 weeks, about 8 weeks, about 6 weeks, about 4 weeks, about 2 weeks, about 1 week, about 5 days, about 72 hours, about 48 hours, about 24 hours, about 12 hours, about 8 hours, about 4 hours, or about 2 hours or less of the previous dose. In one embodiment, ISS are administered at intervals ranging from at least every two weeks to every four weeks (e.g., monthly intervals) in order to maintain the maximal desired therapeutic effect (e.g., to provide for maintenance of relief from BD-associated symptoms).

Regenerative Medicine

According to the present invention, somatic cells can be provided that are capable as serving as a primitive organ-like structure comprised of a plurality of types of somatic cell types.

Somatic cells as referred to in the present invention refer to cells that have reached differentiation into cells that compose various organs of the body, and refer to cells that are the opposite of undifferentiated stem cells. The present invention is characterized by the use of two or more somatic cells, and preferably consists of various combinations thereof, such as a combination of an epithelial cell line and mesenchymal cells, a combination of endothelial cells and mesenchymal cells, or a combination of epithelial cells and mesenchymal cells.

There are no particular limitations on organs capable of being formed by the somatic cells as claimed in the present invention, examples of which include various organs such as hair follicle, lung, kidney, liver, pancreas, spleen, heart, gallbladder, small intestine, colon, large intestine, joint, bone, tooth, blood vessel, lymph duct, cornea, cartilage, olfactory organ or auditory organ.

Various mammals can be used without limitation as the origin of the cells as claimed in the present invention corresponding to the purpose thereof, examples of which include chimpanzees, other primates, domestic animals such as dogs or cats, farm animals such as cows, pigs, horses, sheep or goats, laboratory animals such as rabbits, rats, mice or guinea pigs, and more preferably nude mice, SCID mice or nude rats. In addition, although combinations thereof may be homogeneous combinations or heterogeneous combinations, homogeneous combinations are preferable.

The present invention is characterized by the addition of a Wnt/β-catenin signaling pathway activator according to Formulas I, II or III to a mixture of types of differentiated somatic cells as described above followed by culturing thereof. Wnt signaling refers to a series of actions that demonstrate the function of transcription factors by promoting nuclear migration of β-catenin. These signals originate from cellular interaction that includes, for example, a series of processes in which a protein referred to as Wnt3A secreted from certain cells further acts on other cells causing nuclear migration of intracellular β-catenin which acts as a transcription factor. This series of processes give rise to the initial phenomenon of organ construction in the example of epithelial-mesenchymal interaction. The Wnt/β-catenin signaling pathway is known to control cell proliferation and differentiation, organ formation and various cell functions such as cell migration during initial development. Although Wnt signaling is used when culturing ES cells for the purpose of inhibiting differentiation due to their function of maintaining an undifferentiated state, their utilization and effects during culturing of somatic cells are completely unknown.

Another characteristic of the present invention is the subjecting of the mixture of types of differentiated somatic cells, to which a compound according to Formulas I, II or III has been added, to non-plate contact culturing. Non-plate contact culturing refers to a method of culturing cells on an interface having a spherical surface so as not to allow adhesion of plate-adhering cells. An example of non-plate contact culturing is a hanging drop method. The hanging drop method refers to adhering a drop of culture medium containing cultured cells onto the inside of the upper lid of a culture dish, carefully closing the lid so that the culture medium does not drop or run down, and culturing cells within the culture medium to be cultured in the form of an inverted drop due to surface tension. As a result of culturing in this manner, the effects on the cells attributable to contact with a flat surface as in the case of plate culturing can be minimized. Other examples of non-plate contact culturing methods include a formation method utilizing a semi-spherical cell culture dish that has been surface-treated in advance to prevent cell adhesion (for example, "Spheroid" commercially available from Sumitomo Bakelite) (referred to as the spheroid formation method), and a suspension method in which cells are aggregated in a suspended state by culturing in a nitrocellulose medium.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a Wnt pathway activator as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

In this specification and in the claims, the following terms have the meanings as defined. As used herein, "alkyl" means a branched, or straight chain chemical group containing only carbon and hydrogen, such as methyl, isopropyl, isobutyl, sec-butyl and pentyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C═C— or —C≡C— subunits), at one or several positions. Typically, alkyl groups will comprise 1 to 9 carbon atoms, preferably 1 to 6, and more preferably 1 to 4 carbon atoms.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Typically, carbocyclyl groups will comprise 3 to 10 carbon atoms, preferably 3 to 6.

As used herein, "lower alkyl" means a subset of alkyl, and thus is a hydrocarbon substituent, which is linear, or branched. Preferred lower alkyls are of 1 to about 4 carbons, and may be branched or linear. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "amido" means a H—CON— or alkyl-CON—, carbocyclyl-CON—, aryl-CON—, heteroaryl-CON— or heterocyclyl-CON group wherein the alkyl, carbocyclyl, aryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., amino, cyano, hydroxyl, lower alkyl, haloalkyl, alkoxy, nitro, halo, mercapto, and other substituents. A preferred carbocyclic aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, hydroxyl, lower alkyl, haloalkyl, alkoxy, nitro, halo, mercapto, and other substituents. Examples of heteroaryl include thienyl, pyrridyl, furyl, oxazolyl, oxadiazolyl, pyrollyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl and others.

In these definitions it is clearly contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, cycloalkyl, hydroxy, alkoxy, cyano, halo, haloalkyl, mercapto and the like.

As used herein, "amide" includes both RNR'CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, carbocyclyl-CO—, aryl-CO—, heteroaryl-CO— or heterocyclyl-CO— group wherein the alkyl, carbocyclyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo or halide" is a chloro, bromo, fluoro or iodo atom radical. Chloro, bromo and fluoro are preferred halides. The term "halo" also contemplates terms sometimes referred to as "halogen", or "halide".

As used herein, "haloalkyl" means a hydrocarbon substituent, which is linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 3 carbons in length, more preferred haloalkyls are 1 to about 2 carbons, and most preferred are 1 carbon in length. The skilled artisan will recognize then that as used herein, "haloalkylene" means a diradical variant of haloalkyl, such diradicals may act as spacers between radicals, other atoms, or between the parent ring and another functional group.

As used herein, "heterocyclyl" means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls may be substituted or unsubstituted with one or more substituents, e.g., halogen, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. More preferred heterocycles are of 5-7 members. In six membered monocyclic heterocycles, the heteroatom(s) are selected from one up to three of O, N or S, and wherein when the heterocycle is five membered, preferably it has one or two heteroatoms selected from O, N, or S.

As used herein, "substituted amino" means an amino radical which is substituted by one or two alkyl, cycloalkyl, aryl, heteroaryl or heterocyclyl groups, wherein the alkyl, aryl, heteroaryl or heterocyclyl are defined as above.

As used herein, "substituted thiol" means RS— group wherein R is an alkyl, an aryl, heteroaryl or a heterocyclyl group, wherein the alkyl, cycloalkyl, aryl, heteroaryl or heterocyclyl are defined as above.

As used herein, "sulfonyl" means an alkylSO$_2$, arylSO$_2$, heteroarylSO$_2$, carbocyclylSO$_2$, or heterocyclyl-SO$_2$ group wherein the alkyl, carbocyclyl, aryl, heteroaryl or heterocyclyl are defined as above.

As used herein, "sulfamido" means an alkyl-N—S(O)$_2$N—, aryl-NS(O)$_2$N—, heteroaryl-NS(O)$_2$N—, carbocyclyl-NS(O)$_2$N or heterocyclyl-NS(O)$_2$N— group wherein the alkyl, carbocyclyl, aryl, heteroaryl or heterocyclyl group is as herein described.

As used herein, "sulfonamido" means an alkyl-S(O)$_2$N—, aryl-S(O)$_2$N—, heteroaryl-S(O)$_2$N—, carbocyclyl-S(O)$_2$N— or heterocyclyl-S(O)$_2$N— group wherein the alkyl, carbocyclyl, aryl, heteroaryl or heterocyclyl group is as herein described.

As used herein, "ureido" means an alkyl-NCON—, aryl-NCON—, heteroaryl-NCON—, carbocyclyl-NCON— or heterocyclyl-NCON— group wherein the alkyl, carbocyclyl, aryl, heteroaryl or heterocyclyl group is as herein described.

As used herein, when two groups are indicated to be "linked" or "bonded" to form a "ring," it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic, carbocyclic, aryl, or heteroaryl rings.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this invention, though such resonance forms or tautomers are not represented herein.

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of giving a dosage of a compound or pharmaceutical composition to a vertebrate or invertebrate, including a mammal, a bird, a fish, or an amphibian, where the method is, e.g., intrarespiratory, topical, oral, intravenous, intraperitoneal, intramuscular, buccal, rectal, sublingual. The preferred method of administration can vary depending on various factors, e.g., the components of the pharmaceutical composition, the site of the disease, the disease involved, and the severity of the disease.

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, monkeys, dogs, and cats, but also includes many other species.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2006); *Goodman and Gilman's: The Pharmacological Basis of Therapeutics,* 11th Ed., The McGraw-Hill Companies.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in World Patent Publication 87/05297, Johnston et al., published Sep. 11, 1987 (incorporated by reference herein).

"Solvate" refers to the compound formed by the interaction of a solvent and a Wnt pathway inhibitor, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

By "therapeutically effective amount" or "pharmaceutically effective amount" is typically one which is sufficient to achieve the desired effect and may vary according to the nature and severity of the disease condition, and the potency of the compound. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and includes curing a disease. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a pharmaceutical composition for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

The expression "drug-eluting" shall be understood to refer to any and all mechanisms, e.g., diffusion, migration, permeation, and/or desorption by which the drug(s) incorporated in the drug-eluting material pass therefrom over time into the surrounding body tissue.

The expression "drug-eluting material" shall be understood herein to mean any natural, synthetic or semi-synthetic material capable of acquiring and retaining a desired shape or configuration and into which one or more drugs can be incorporated and from which incorporated drug(s) are capable of eluting over time.

The expression "elutable drug" shall be understood to mean any drug or combination of drugs having the ability to pass over time from the drug-eluting material in which it is incorporated into the surrounding areas of the body.

The following abbreviations have the indicated meanings:
Aβ=amyloid beta
ACE=angiotensin I-converting enzyme
AD=Alzheimer's disease
ALS=amyotrophic Lateral Sclerosis
AMD=age related macular degeneration
APC=adenomatous polyposis coli
β-TrCP=β-transducin repeat-containing protein
CD44=cell-surface glycoprotein
CK1,2=casein kinase 1 and 2
DHT=dihydrotestosterone
Dkk=dickkopf
DME=diabetic macular edema
Dsh/Dvl=dishevelled
EphB2=ephrin type-B receptor 2
ES cells=embryonic stem cells
FTD=frontotemporal Dementia
Fzd=frizzled
GBP=GSK-3 binding protein
GI=gastrointestinal
GPCR=G protein-coupled receptor
GSK-3=glycogen synthase kinase-3
HCC=hepatocellular carcinoma
IBD=inflammatory bowel disease
Kr2=kringle domain 2
L-DOPA=L-3,4-dihydroxyphenylalanine
Lef=lymphoid enhancing factor
LRP=low density lipoprotein receptor related protein
MMTV=mouse mammary tumor virus
PD=Parkinson's disease
PKC=protein kinase C
PI-3=phosphatidylinositol-3 kinase
PPAR=peroxisome proliferator-activated receptors
PTEN=phosphatase and tensin homolog
RP=retinitis pigmentosa
SCID=severe combined immunodeficiency
SOD1=Superoxide dismutase protein
SOST=sclerostin
sFRP=secreted frizzled-related protein
TCF=T-cell factor
TGF=transforming growth factor
UC=ulcerative colitis
Wg=wingless
Wnt=wingless-type MMTV integration site family member Compounds The compounds and compositions described herein are capable of activating the Wnt/β-catenin signaling pathway. The Wnt/β-catenin signaling pathway has been found to play a crucial role in the differentiation and development of nerve cells for the central nervous system, bone formation, hair follicle development and regeneration, and stimulation of stem cell growth, maintenance and differentiation. Such compounds and compositions are therefore expected to be useful against cell proliferation disorders, bone disorders, Alzheimer's disease and even tissue generation.

Some embodiments of the present invention include compounds, salts, pharmaceutically acceptable salts or pro-drug thereof of formula (I):

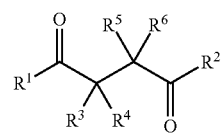

In some embodiments, $R^1$ is selected from the group consisting of substituted or unsubstituted heteroaryl and substituted or unsubstituted heterocyclyl, with the proviso that a carbon atom is attached to the carbonyl.

In some embodiments, $R^2$ is selected from the group consisting of substituted or unsubstituted aryl, substituted or unsubstituted heteroaryl, substituted or unsubstituted carbocyclyl and substituted or unsubstituted heterocyclyl, with the proviso that a carbon atom is attached to the carbonyl.

In some embodiments, $R^3$, $R^4$, $R^5$ and $R^6$ are independently selected from a group consisting of H, —$C_{1-9}$alkyl, —$C_{1-9}$alkylaryl and —$C_{1-9}$alkylheteroaryl.

In more specific embodiments, $R^1$ is selected from the group consisting of

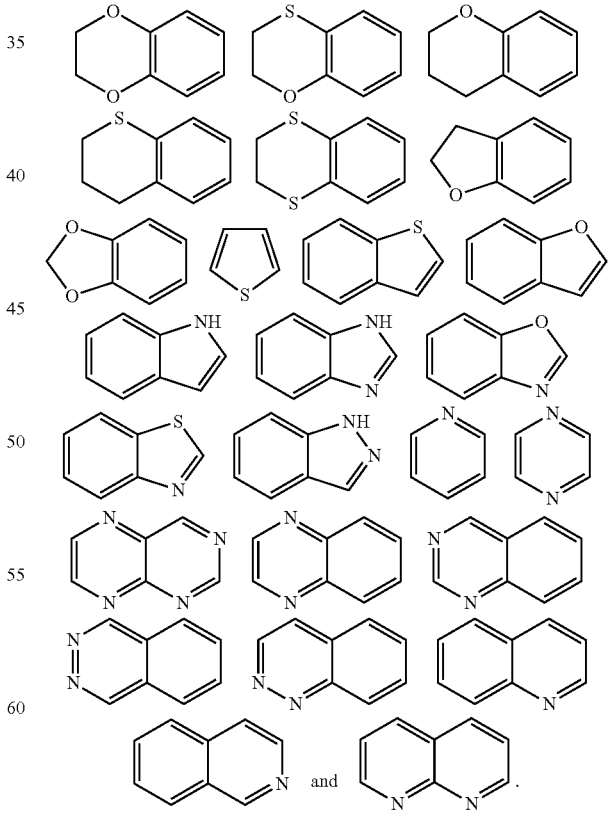

In another specific embodiments, $R^2$ is selected from the group consisting of substituted or unsubstituted aryl,

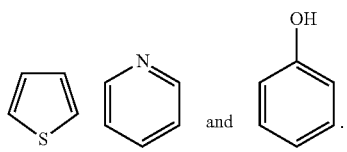 and 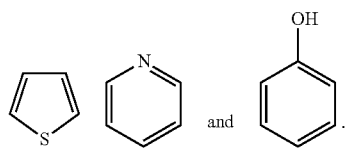

In another specific embodiments, $R^3$, $R^4$, $R^5$ and $R^6$ are H.

Some embodiments of the present invention include compounds, salts, pharmaceutically acceptable salts or pro-drug thereof of formula (II):

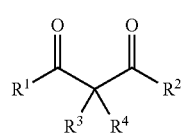

II

In some embodiments, $R^1$ is selected from the group consisting of substituted or unsubstituted heteroaryl and substituted or unsubstituted heterocyclyl, with the proviso that a carbon atom is attached to the carbonyl.

In some embodiments, $R^2$ is selected from the group consisting of substituted or unsubstituted aryl, substituted or unsubstituted heteroaryl, substituted or unsubstituted carbocyclyl and substituted or unsubstituted heterocyclyl, with the proviso that a carbon atom is attached to the carbonyl.

In some embodiments, $R^3$ and $R^4$ are independently selected from a group consisting of H, —$C_{1-9}$alkyl, —$C_{1-9}$alkylaryl and —$C_{1-9}$alkylheteroaryl.

In more specific embodiments, $R^1$ is selected from the group consisting of

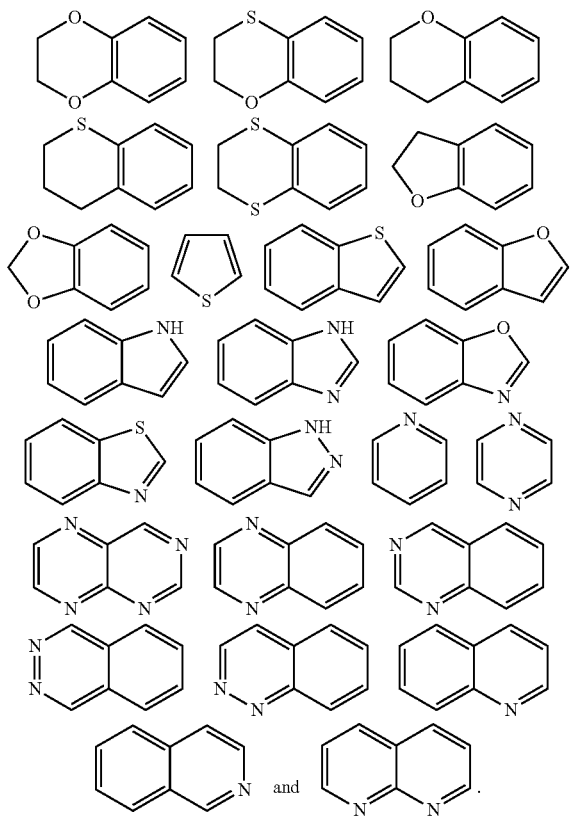

In another specific embodiments, $R^2$ is selected from the group consisting of substituted or unsubstituted aryl, In another specific embodiments, $R^3$ and $R^4$ are H.

Some embodiments of the present invention include compounds, salts, pharmaceutically acceptable salts or pro-drug thereof of formula (III):

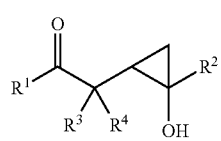

III

In some embodiments, $R^1$ is selected from the group consisting of substituted or unsubstituted aryl, substituted or unsubstituted heteroaryl, substituted or unsubstituted carbocyclyl and substituted or unsubstituted heterocyclyl, with the proviso that a carbon atom is attached to the carbonyl.

In some embodiments, $R^2$ is selected from the group consisting of substituted or unsubstituted aryl, substituted or unsubstituted heteroaryl, substituted or unsubstituted carbocyclyl and substituted or unsubstituted heterocyclyl, with the proviso that a carbon atom is attached to the carbonyl.

In some embodiments, $R^3$ and $R^4$ are independently selected from a group consisting of H, —$C_{1-9}$alkyl, —$C_{1-9}$alkylaryl and —$C_{1-9}$alkylheteroaryl.

Illustrative compounds of Formulas I, II and III are shown in Table 1.

TABLE 1

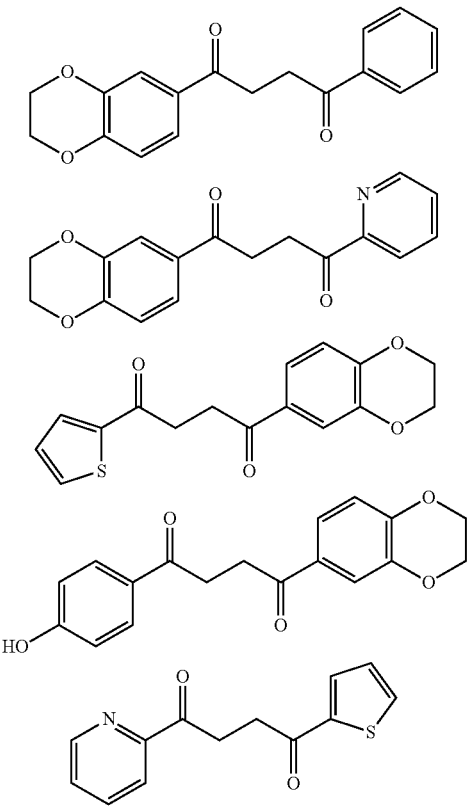

TABLE 1-continued

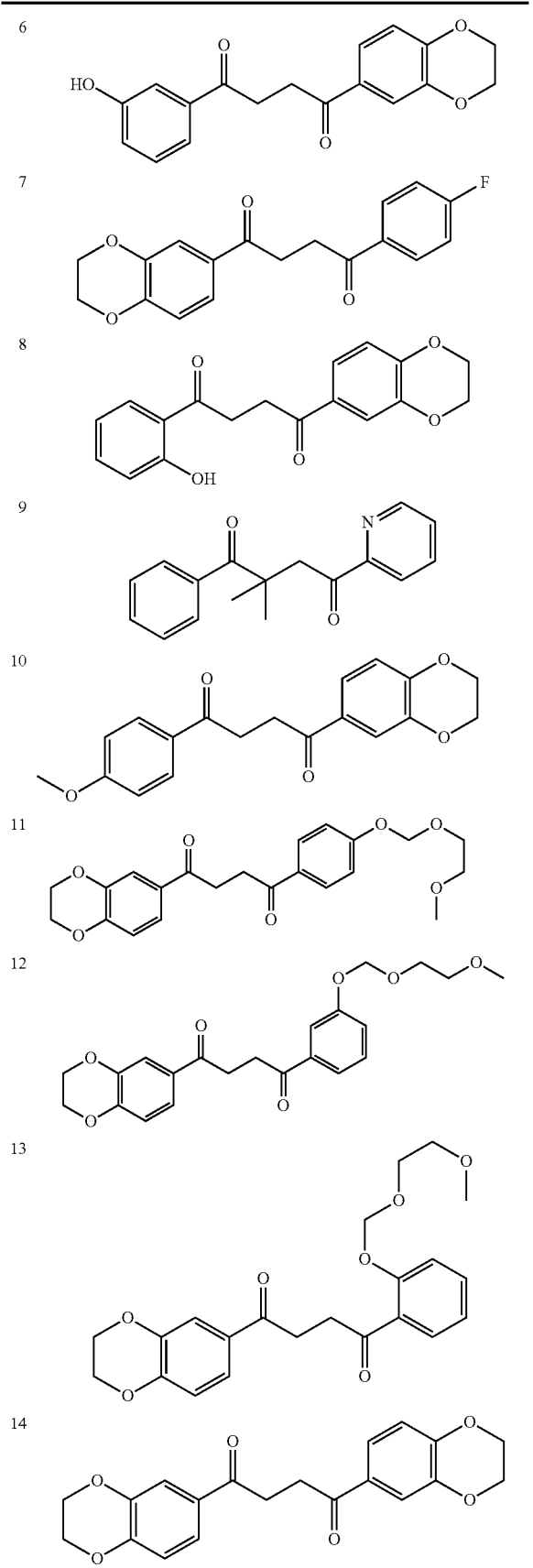

TABLE 1-continued

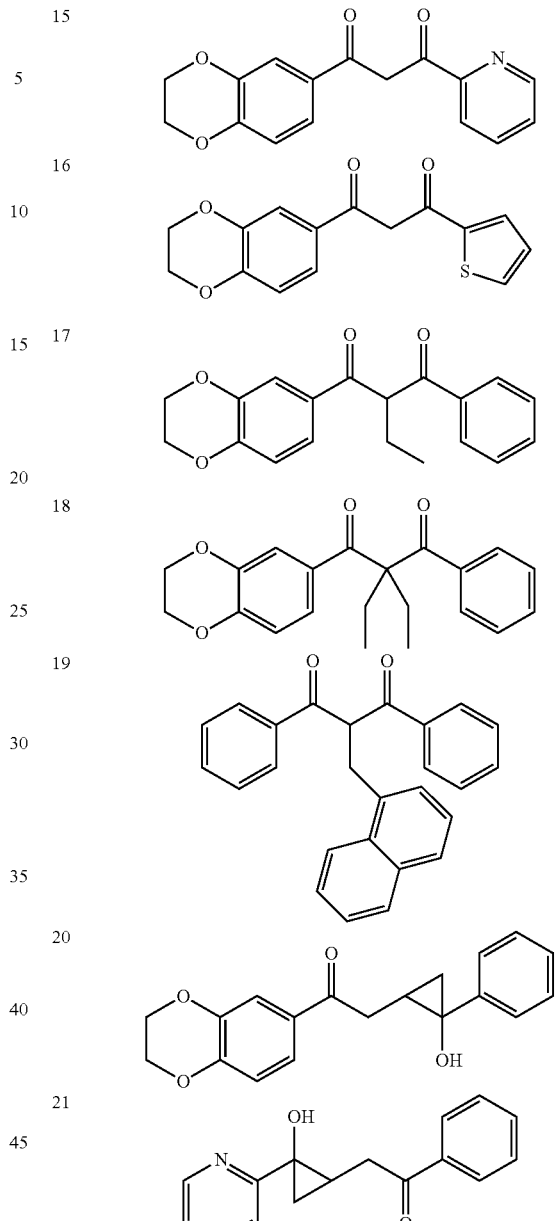

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 6th Ed., John Wiley & Sons (2007), Carey and Sundberg, *Advanced Organic Chemistry* 5th Ed., Springer (2007), *Comprehensive Organic Transformations: A Guide to Functional Group Transformations*, 2nd Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis*, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1$H nuclear magnetic resonance spectra (NMR) were measured in the indicated solvents on a Bruker NMR spectrometer (Avance™ DRX300, 300 MHz for 1H). Peak positions are expressed in parts per million (ppm) downfield from tetramethylsilane. The peak multiplicities are denoted as follows, s, singlet; d, doublet; t, triplet; m, multiplet.

The following abbreviations have the indicated meanings
Bi(OTf)$_3$=bismuth(III) triflate
brine=saturated aqueous sodium chloride
CDCl$_3$=deuterated chloroform
DMSO-d$_6$=deuterated dimethylsulfoxide
ESIMS=electron spray mass spectrometry
EtOAc=ethyl acetate
HCl=hydrochloric acid
MgSO$_4$=magnesium sulfate
NaH=sodium hydride
NMR=nuclear magnetic resonance
Ph=phenyl
K$_2$CO$_3$=potassium carbonate
rt=room temperature
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds of the invention will be readily apparent to the person of ordinary skill in the art in light of the following reaction schemes and examples. Unless otherwise indicated, all variables are as defined above.

General Procedures

Compounds of Formula I of the present invention can be prepared as depicted in Scheme 1.

Scheme 1

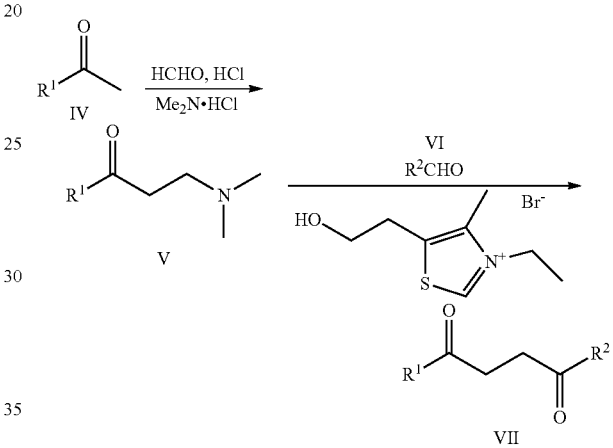

Scheme 1 describes a method for preparation of unsubstituted 1,4-diketones derivatives (VII) by the modified Stetter reaction of a Mannich base as a vinyl ketone precursor with aldehyde. The Mannich base is formed by first reacting a methyl ketone (IV) with paraformaldehyde and dimethylamine hydrochloride to form the 3-dimethylamino-propan-1-one (V). Next, Mannich base (V) was reacted with various aldehydes (VI) under standard Stetter conditions using a thiazolium salt as the catalyst yields unsubstituted 1,4-diketone derivatives (VII).

Compounds of Formula I of the present invention where the alpha and/or beta positions are substituted can be prepared as depicted in Scheme 2.

Scheme 2

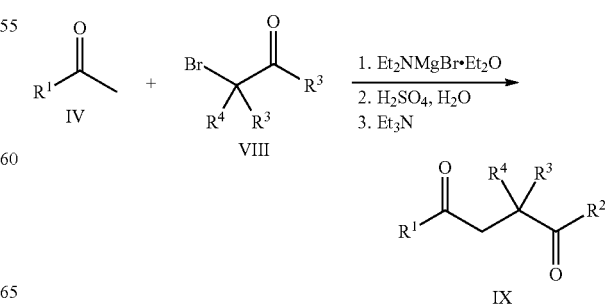

Scheme 2 describes a method for preparation of substituted 1,4-diketones derivatives (IX) by the method of Kel'in and Kulinkovich [*Synthesis* (1996), (3), 330-2] which is based on the application of magnesium reagents in the cross-aldol condensation of methyl ketones with α-bromo ketones. A methyl ketone (IV) is reacted with a substituted α-bromo ketone (VIII) in the presence of diethylamidomagnesium bromide and acid followed by treatment with triethylamine to produce the desired substituted 1,4-diketone derivatives (IX).

Compounds of Formula II of the present invention can be prepared as depicted in Scheme 3.

Scheme 3

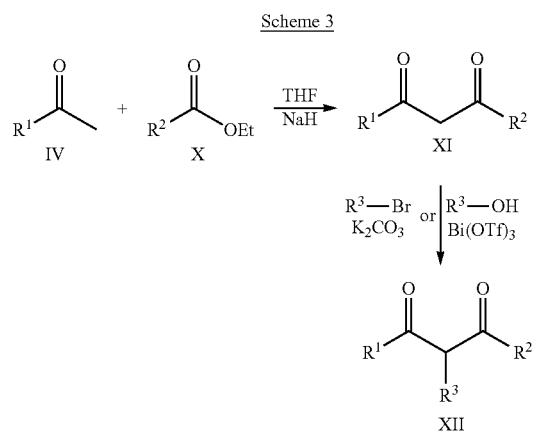

Scheme 3 describes a method for preparation of β-diketone derivatives (VII) by a crossed Claisen condensation. A methyl ketone (IV) is condensed with an ester (X) in the presence of sodium hydride to yield β-diketone derivatives (XI). The α-position can be further substituted with alkylbromides and base or by alkyl alcohols in the presence of a Lewis acid catalyst to yield β-diketone derivatives (XII).

Compounds of Formula III of the present invention can be prepared as depicted in Scheme 4.

Scheme 4

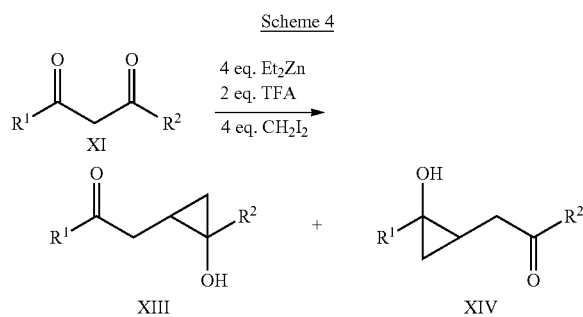

Scheme 4 describes a method for preparation of γ-hydroxyketone derivatives (XIII) by the method of Xue, et al [*Journal of Organic Chemistry* (2006), 71(1), 215-218]. A mixture of zinc species formed from 4.0 equiv of $Et_2Zn$, 2.0 equiv of TFA, and 4.0 equiv of $CH_2I_2$ efficiently converts β-diketones into γ-hydroxyketones. $R^1$ groups containing electron-donating substituents tend to insert the cyclopropane near $R^2$ (XIII) where $R^1$ groups containing electron-withdrawing substituents tend to insert the cyclopropane near $R^1$ (XIV).

ILLUSTRATIVE COMPOUND EXAMPLES

Example 1

Preparation of compound (I) is depicted below in Scheme 5.

Scheme 5

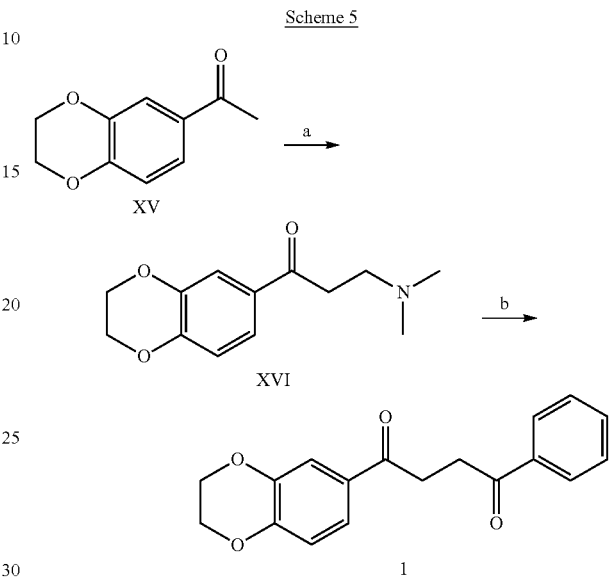

Reagents and conditions: a) Ethanol, HCHO, HCl, refluxed, overnight; b) Dioxane, PhCHO, 3-Ethyl-5-(2-hydroxyethyl)-4-methylthiazolium bromide, 95° C., overnight.

Step a

A solution of 1-(2,3-dihydrobenzo[b][1,4]dioxin-6-yl) ethanone (XV) (11 mmol), dimethylamine hydrochloride (14 mmol), paraformaldehyde (16 mmol) and 12 N HCl (2 drops) in ethanol (5 mL) was refluxed overnight. The solution was cooled to room temperature and the ethanol was evaporated under vacuum. The residue was treated with ethyl acetate, heated slightly and sonicated to disperse into fine particles. The solids were filtered and dried at room temperature to produce 1-(2,3-dihydrobenzo[b][1,4]dioxin-6-yl)-3-(dimethylamino)propan-1-one (XVI) as a white solid, (82% yield), $^1$H NMR ($CDCl_3$, 400 MHz): δ ppm 2.77 (s, 6H), 3.41 (m, 2H), 3.56 (m, 2H), 4.25 (m, 4H), 6.85 (m, 1H), 7.45 (m, 2H).

Step b

Triethylamine (3.61 mmol) and benzaldehyde (4.3 mmol) in dry dioxane (10 mL) was added to a solution of 1-(2,3-dihydrobenzo[b][1,4]dioxin-6-yl)-3-(dimethylamino)propan-1-one (XVI) (5.4 mmol) and 3-ethyl-5-(2-hydroxyethyl)-4-methylthiazolium bromide (0.43 mmol) in dioxane heated at 95° C. under nitrogen. The solution was further heated overnight at 95° C. The solution was cooled and excess solvent was evaporated under vacuum. The residue was partitioned between $CH_2Cl_2$ and water. The organic phase was dried over $MgSO_4$, filtered and concentrated. The residue was purified by flash chromatography eluting with ethyl acetate in hexane gradient to yield 1-(2,3-dihydrobenzo[b][1,4]dioxin-6-yl)-4-phenylbutane-1,4-dione 1 as a white solid (12% yield). $^1$H NMR (DMSO-$d_6$, 400 MHz): δ ppm 3.33-3.37 (m, 4H), 4.29 (m, 2H), 4.34 (m, 2H), 6.98 (m, 1H), 7.48 (m, 1H), 7.55 (m, 3H), 7.64 (m, 1H), 8.00-8.02 (m, 2H); ESIMS found $C_{18}H_{16}O_4$ m/z 297 (M+H).

The following compounds was prepared in accordance with the procedure described in the above Example 1.

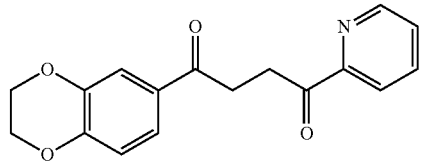 [SMILES: O=C(CCC(=O)c1ccccn1)c1ccc2c(c1)OCCO2]

1-(2,3-dihydrobenzo[b][1,4]dioxin-6-yl)-4-(pyridin-2-yl)butane-1,4-dione 2.

White solid. $^1$H NMR (CDCl$_3$, 400 MHz): δ ppm 3.37 (m, 2H), 3.40 (m, 2H), 4.31 (m, 4H), 6.92 (m, 1H), 7.47 (m, 2H), 7.56 (m, 1H), 7.83 (m, 1H), 8.03 (m, 1H), 8.71 (m, 1H); ESIMS found C$_{17}$H$_{15}$NO$_4$ m/z 298 (M+H).

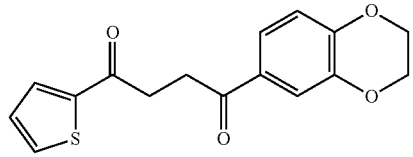 [SMILES: O=C(CCC(=O)c1cccs1)c1ccc2c(c1)OCCO2]

1-(2,3-dihydrobenzo[b][1,4]dioxin-6-yl)-4-(thiophen-2-yl)butane-1,4-dione 3.

Yellow solid. $^1$H NMR (DMSO-d$_6$, 400 MHz): δ ppm 4.29 (m, 2H), 4.34 (m, 2H), 6.97 (m, 1H), 7.25 (m, 1H), 7.47 (m, 1H), 7.52 (m, 1H), 8.00-8.03 (m, 2H); ESIMS found C$_{16}$H$_{14}$O$_4$S m/z 303 (M+H).

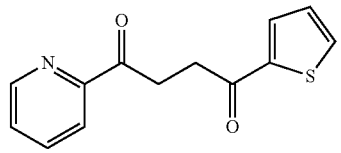 [SMILES: O=C(CCC(=O)c1cccs1)c1ccccn1]

1-(pyridin-2-yl)-4-(thiophen-2-yl)butane-1,4-dione 5.

White solid. $^1$H NMR (DMSO-d$_6$, 400 MHz): δ ppm 3.40 (m, 2H), 3.56 (m, 2H), 7.27 (dd, J=4.8, 3.8 Hz, 1H), 7.70 (m, 1H), 7.95 (d, J=7.8 Hz, 1H), 8.00-8.05 (m, 3H), 8.76 (d, J=4.3 Hz, 1H); ESIMS found C$_{13}$H$_{11}$NO$_2$S m/z 246 (M+H).

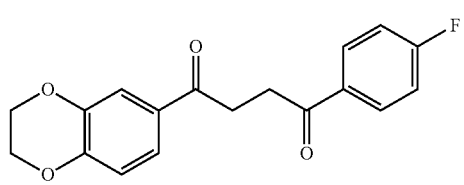

1-(2,3-dihydrobenzo[b][1,4]dioxin-6-yl)-4-(4-fluorophenyl)butane-1,4-dione 7.

Off white solid. $^1$H NMR (CDCl$_3$, 400 MHz): δ ppm 3.40 (s, 4H), 4.30 (m, 4H), 6.92 (m, 1H), 7.16 (m, 2H), 7.57 (m, 2H), 8.04 (m, 2H); ESIMS found C$_{18}$H$_{15}$FO$_4$ m/z 315 (M+H).

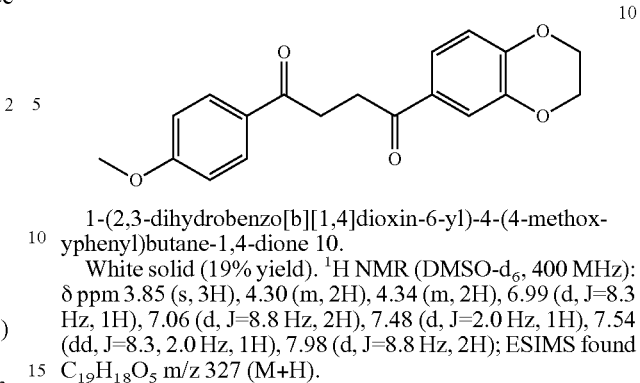

1-(2,3-dihydrobenzo[b][1,4]dioxin-6-yl)-4-(4-methoxyphenyl)butane-1,4-dione 10.

White solid (19% yield). $^1$H NMR (DMSO-d$_6$, 400 MHz): δ ppm 3.85 (s, 3H), 4.30 (m, 2H), 4.34 (m, 2H), 6.99 (d, J=8.3 Hz, 1H), 7.06 (d, J=8.8 Hz, 2H), 7.48 (d, J=2.0 Hz, 1H), 7.54 (dd, J=8.3, 2.0 Hz, 1H), 7.98 (d, J=8.8 Hz, 2H); ESIMS found C$_{19}$H$_{18}$O$_5$ m/z 327 (M+H).

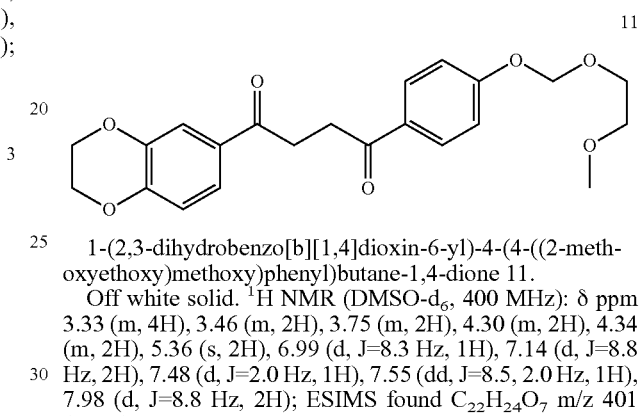

1-(2,3-dihydrobenzo[b][1,4]dioxin-6-yl)-4-(4-((2-methoxyethoxy)methoxy)phenyl)butane-1,4-dione 11.

Off white solid. $^1$H NMR (DMSO-d$_6$, 400 MHz): δ ppm 3.33 (m, 4H), 3.46 (m, 2H), 3.75 (m, 2H), 4.30 (m, 2H), 4.34 (m, 2H), 5.36 (s, 2H), 6.99 (d, J=8.3 Hz, 1H), 7.14 (d, J=8.8 Hz, 2H), 7.48 (d, J=2.0 Hz, 1H), 7.55 (dd, J=8.5, 2.0 Hz, 1H), 7.98 (d, J=8.8 Hz, 2H); ESIMS found C$_{22}$H$_{24}$O$_7$ m/z 401 (M+H).

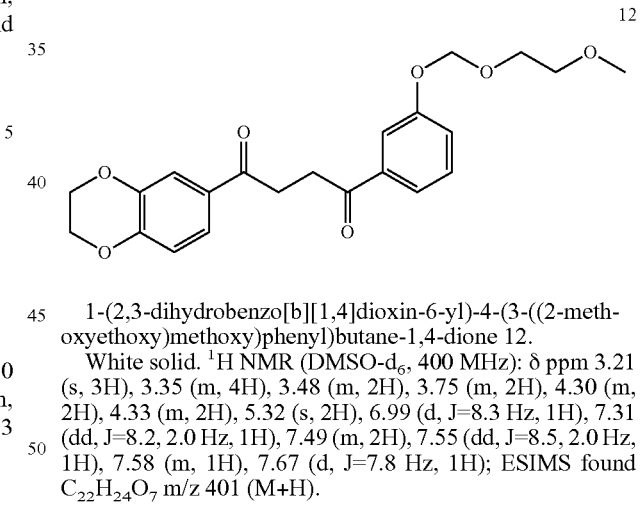

1-(2,3-dihydrobenzo[b][1,4]dioxin-6-yl)-4-(3-((2-methoxyethoxy)methoxy)phenyl)butane-1,4-dione 12.

White solid. $^1$H NMR (DMSO-d$_6$, 400 MHz): δ ppm 3.21 (s, 3H), 3.35 (m, 4H), 3.48 (m, 2H), 3.75 (m, 2H), 4.30 (m, 2H), 4.33 (m, 2H), 5.32 (s, 2H), 6.99 (d, J=8.3 Hz, 1H), 7.31 (dd, J=8.2, 2.0 Hz, 1H), 7.49 (m, 2H), 7.55 (dd, J=8.5, 2.0 Hz, 1H), 7.58 (m, 1H), 7.67 (d, J=7.8 Hz, 1H); ESIMS found C$_{22}$H$_{24}$O$_7$ m/z 401 (M+H).

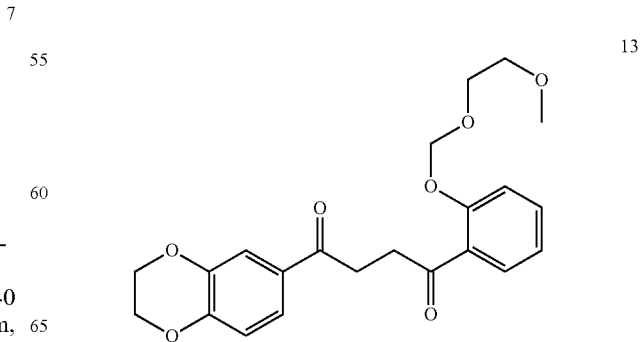

1-(2,3-dihydrobenzo[b][1,4]dioxin-6-yl)-4-(2-((2-methoxyethoxy)methoxy)phenyl)butane-1,4-dione 13.

Viscous oil (14% Yield). $^1$H NMR (DMSO-d$_6$, 400 MHz): δ ppm 3.21 (s, 3H), 3.25-3.29 (m, 4H), 3.46-3.48 (m, 2H), 3.79 (m, 2H), 4.29 (m, 2H), 4.33 (m, 2H), 5.39 (s, 2H), 6.98 (d, J=8.6 Hz, 1H), 7.10 (m, 1H), 7.25 (dd, J=8.3 Hz, 1H), 7.47 (m, 1H), 7.49-7.54 (m, 2H), 7.58 (dd, J=7.7, 1.6 Hz, 1H); ESIMS found C$_{22}$H$_{24}$O$_7$ m/z 401 (M+H).

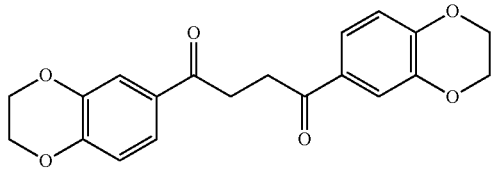

14

1,4-bis(2,3-dihydrobenzo[b][1,4]dioxin-6-yl)butane-1,4-dione 14.

Off white solid. $^1$H NMR (CDCl$_3$, 400 MHz): δ ppm 3.35 (s, 4H), 4.30 (m, 8H), 6.92 (m, 2H), 7.57 (m, 4H); ESIMS found C$_{20}$H$_{18}$O$_6$ m/z 355 (M+H).

Example 2

Preparation of compound (4) is depicted below in Scheme 6.

Scheme 6

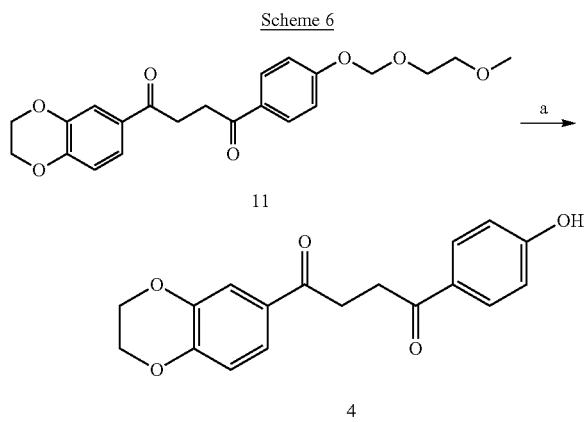

Reagents and conditions: a) CH$_2$Cl$_2$, TFA, rt, overnight.

Step a

Neat TFA (0.5 mL) was added to a solution of 1-(2,3-dihydrobenzo[b][1,4]dioxin-6-yl)-4-(4-((2-methoxyethoxy)methoxy)phenyl)butane-1,4-dione 11 (0.35 mmol) in CH$_2$Cl$_2$ (5 mL) stirred at room temperature. The solution was further stirred overnight at room temperature. The volatiles were evaporated under vacuum. The residue was purified by flash chromatography over silica gel eluting with 1% methanol in CH$_2$Cl$_2$ to get 1-(2,3-dihydrobenzo[b][1,4]dioxin-6-yl)-4-(4-hydroxyphenyl)butane-1,4-dione 4 as an off white solid (21% yield). $^1$H NMR (CDCl$_3$, 400 MHz): δ ppm 3.37 (m, 4H), 4.29 (m, 2H), 4.33 (m, 2H), 5.76 (s, 1H), 6.87 (d, J=8.8 Hz, 2H), 6.93 (m, 1H), 7.60 (m, 2H), 7.94 (d, J=8.8 Hz, 2H); ESIMS found C$_{18}$H$_{16}$O$_5$ m/z 313 (M+H).

The following compounds was prepared in accordance with the procedure described in the above Example 2.

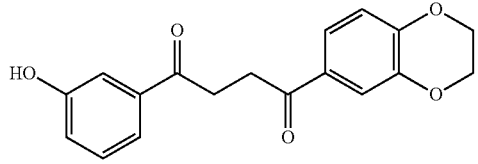 [SMILES: O=C(CCC(=O)c1ccc2c(c1)OCCO2)c1cccc(O)c1]

6

1-(2,3-dihydrobenzo[b][1,4]dioxin-6-yl)-4-(3-hydroxyphenyl)butane-1,4-dione 6.

Off white solid (27% yield). $^1$H NMR (DMSO-d6, 400 MHz): δ ppm 3.27 (m, 4H), 4.30 (m, 2H), 4.34 (m, 2H), 6.99 (d, J=8.8 Hz, 1H), 7.03 (d, J=8.8 Hz, 1H), 7.36 (m, 2H), 7.45 (m, 2H), 7.54 (d, J=8.8 Hz, 1H).

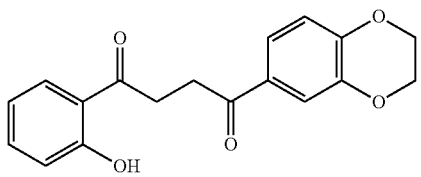 [SMILES: O=C(CCC(=O)c1ccccc1O)c1ccc2c(c1)OCCO2]

8

1-(2,3-dihydrobenzo[b][1,4]dioxin-6-yl)-4-(2-hydroxyphenyl)butane-1,4-dione 8.

Off white solid (62% yield). $^1$H NMR (DMSO-d6, 400 MHz): δ ppm 3.43 (m, 4H), 4.00 (m, 4H), 4.34 (m, 2H), 6.96 (m, 3H), 7.48-7.56 (m, 3H), 7.97 (m, 1H).

Example 3

Preparation of compound (9) is depicted below in Scheme 7.

Scheme 7

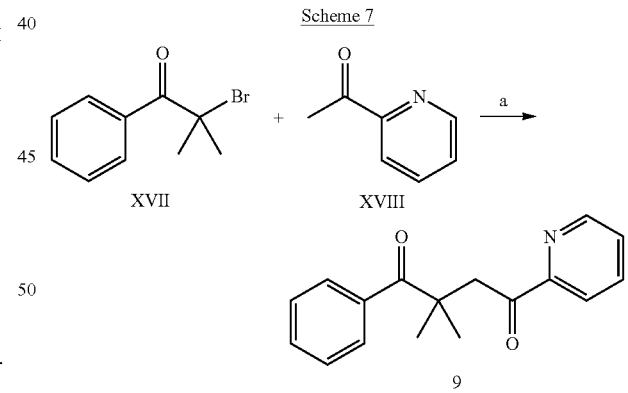

Reagents and conditions: a) i) Et$_2$NMgBLEt$_2$O, Toluene, 0° C., 3 h ii) H$_2$SO$_4$, H$_2$O, 0° C.-rt, iii) Et$_3$N, rt.

Step a

In a dried 3 neck flask fitted with magnetic stirrer and condensor was placed metal magnesium (12 mmol) and ether (1.8 mL). Neat bromoethane (2.5 mmol) was added via syringe and the reaction was started immediately. A solution of bromoethane (10.5 mmol) in toluene (30 mL) was added to the solution slowly. After completion of the addition, the solution was stirred at room temperature for 30 min under nitrogen before adding neat diethylamine (24 mmol). The solution was further stirred at room temperature for 15 min.

The solution was cooled to 0° C. and a mixture of 1-(pyridin-2-yl)ethanone (XVIII) (12 mmol) and 2-bromoisobutyrophenone (XVII) (13 mmol) was added to the solution. The solution was further stirred for 3 h at 0° C. under nitrogen. Aqueous 5% $H_2SO_4$ (20 mL) was added to the solution and the solution was warmed to room temperatue. The organic layer was separated, dried over $MgSO_4$ and filtered. The organic layer was then treated with $Et_3N$ (10 mmol) and allowed to stir overnight at room temperature. The solution was then washed with water, dried over $MgSO_4$, filtered and concentrated. The residue was purified by flash chromatography eluting with 1-5% EtOAc in hexane gradient to give 2,2-dimethyl-1-phenyl-4-(pyridin-2-yl)butane-1,4-dione 9 as a colorless viscous oil (11% yield). $^1$H NMR (CDCl$_3$, 400 MHz): δ ppm 1.47 (s, 6H), 3.80 (s, 2H), 7.34-7.50 (m, 4H), 7.65-7.75 (m, 2H), 7.80 (m, 1H), 7.94 (m, 1H), 8.67 (m, 1H); ESIMS found $C_{17}H_{17}NO_2$ m/z 268 (M+H).

Example 4

Preparation of compound (15) is depicted below in Scheme 8.

Scheme 8

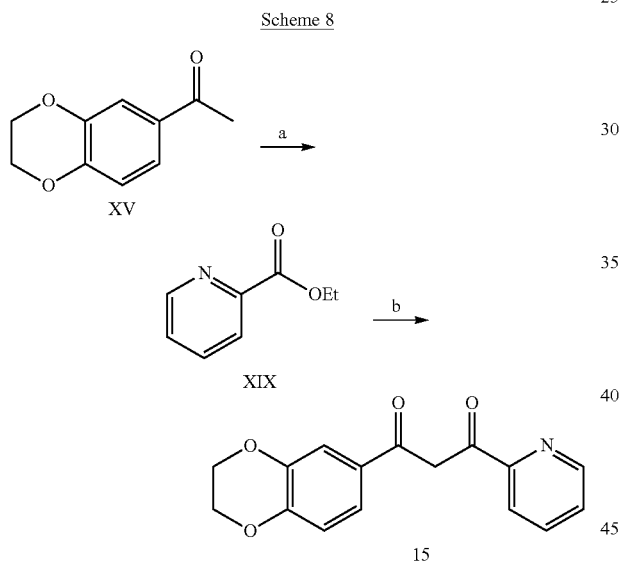

15

Reagents and conditions: a) THF, NaH, rt-reflux, overnight.
Step a
A solution of 1-(2,3-dihydrobenzo[b][1,4]dioxin-6-yl) ethanone (XV) (1 eq) in THF was added slowly to a suspension of NaH (1.5 eq) in THF stirred under nitrogen at room temperature. The solution was further allowed to stir at room temperature until the evolution of gas was ceased. Ethyl picolinate (XIX) (1.1 eq) was added to the solution and refluxed overnight under nitrogen. The solution was cooled, poured into ice water and extracted with ethyl acetate. The organic layer was dried over $MgSO_4$, filtered and concentrated under vacuum. The crude product was purified by column chromatography over silica gel to produce 1-(2,3-dihydrobenzo[b][1,4]dioxin-6-yl)-3-(pyridin-2-yl)propane-1,3-dione 15 as a yellow solid (71% yield), $^1$H NMR (CDCl$_3$, 400 MHz): δ ppm 4.13-4.43 (m, 4H), 6.94 (d, J=8.31 Hz, 1H), 7.42 (m, 1H), 7.44 (m, 1H) 7.59 (m, 2H), 7.85 (m, 1H), 8.14 (d, J=7.81, 1H), 8.65 (m, 1H); ESIMS found $C_{16}H_{13}NO_4$ m/z 284 (M+H).

The following compounds was prepared in accordance with the procedure described in the above Example 4.

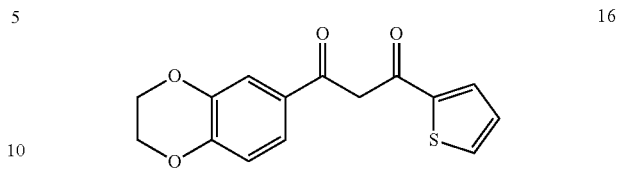

1-(2,3-dihydrobenzo[b][1,4]dioxin-6-yl)-3-(thiophen-2-yl)propane-1,3-dione 16.
Yellow solid. $^1$H NMR (DMSO-d$_6$, 400 MHz): δ ppm 4.34 (m, 4H), 6.98 (m, 1H), 7.15 (br. s, 1H), 7.59 (m, 1H), 7.64 (m, 2H), 8.01 (m, 1H), 8.28 (m, 1H); ESIMS found $C_{15}H_{12}O_4S$ m/z 289 (M+H).

Example 5

Preparation of compounds (17) and (18) are depicted below in Scheme 9.

Scheme 9

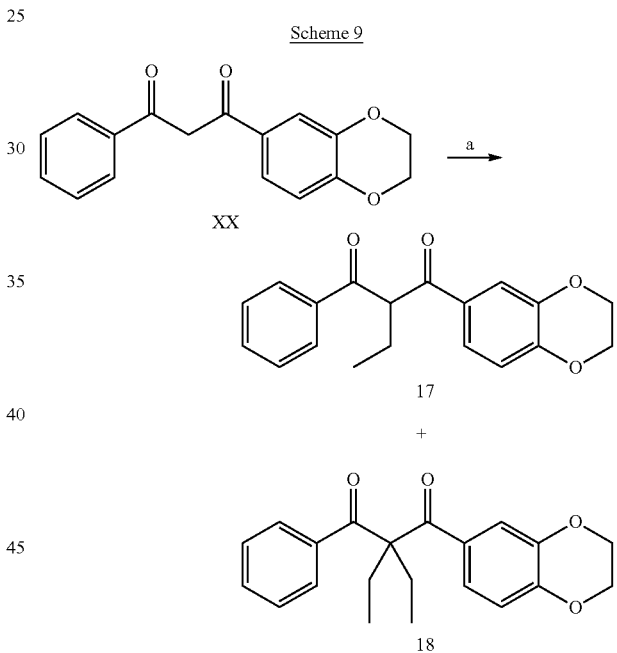

Reagents and conditions: a) DMSO, bromoethane, $K_2CO_3$, rt, overnight.
Step a
Bromoethane (0.87 mmol) was added slowly to a solution 1-(2,3-dihydrobenzo[b][1,4]dioxin-6-yl)-3-phenylpropane-1,3-dione (XX) (0.39 mmol) and $K_2CO_3$ (1.58 mmol) in DMSO (4 mL) stirred at room temperature under nitrogen. The solution was further stirred overnight at room temperature under nitrogen. The solution was poured into a mixture of water and ether. The etheric layer was separated, washed with brine, dried over $MgSO_4$, filtered and concentrated. The residue was purified by column chromatography to get 1-(2,3-dihydrobenzo[b][1,4]dioxin-6-yl)-2-ethyl-3-phenylpropane-1,3-dione 17 as colorless viscous oil (35% yield). $^1$H NMR (DMSO-d$_6$, 400 MHz): δ ppm 0.93 (t, J=7.4 Hz, 3H), 1.93 (m, 2H), 4.28 (m, 2H), 4.33 (m, 2H), 5.60 (t, J=6.5 Hz, 1H), 6.99 (d, J=8.6 Hz, 1H), 7.51-7.55 (m, 4H), 7.66 (m, 1H), 7.98 (d, J=7.3 Hz, 2H); ESIMS found $C_{19}H_{18}O_4$ m/z 311 (M+H) and 1-(2,3-dihydrobenzo[b][1,4]dioxin-6-yl)-2,2-diethyl-3-phenylpropane-1,3-dione 18 as a white solids. ESIMS found $C_{21}H_{22}O_4$ m/z 339 (M+H).

Example 6

Preparation of compound (19) is depicted below in Scheme 10.

Scheme 10

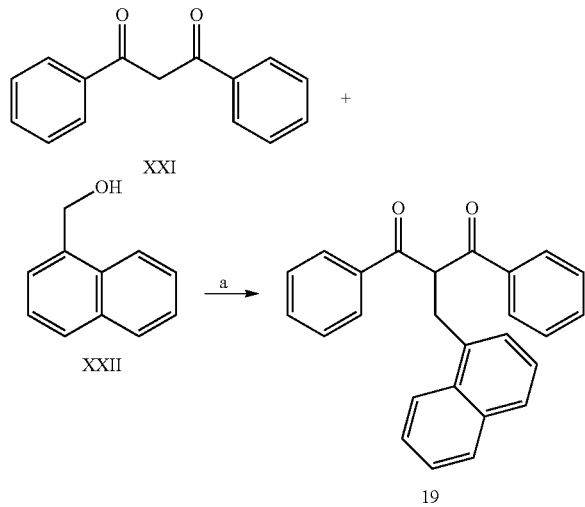

Reagents and conditions: a) $CH_3NO_2$, $Bi(OTf)_3$, 100° C., 2 h
Step a

A solution of naphthalen-1-ylmethanol (XXII) (0.75 mmol) in $CH_3NO_2$ (1 mL) was added slowly over a period of 45 min to a solution of dibenzoylmethane (XXI) (2.27 mmol) and $Bi(OTf)_2$ (0.008 mmol) in $CH_3NO_2$ heated at 100° C. The solution was further stirred at 100° C. for 2 h. The solution was cooled and the solvent was removed under vacuum. The residue was purified by column chromatography to produce 2-(naphthalen-1-ylmethyl)-1,3-diphenylpropane-1,3-dione 19 as a yellow solid (75% yield). $^1$H NMR (DMSO-$d_6$, 400 MHz): δ ppm 3.75 (d, J=7 Hz, 2H), 6.23 (t, J=7 Hz, 1H), 7.24-7.38 (m, 6H), 7.50-7.55 (m, 4H), 7.57 (m, 1H), 7.81-7.87 (m, 5H), 8.14 (m, 1H); ESIMS found $C_{26}H_{20}O_2$ m/z 365 (M+H).

Administration and Pharmaceutical Compositions

Some embodiments include pharmaceutical compositions comprising: (a) a safe and therapeutically effective amount of a compound according to Formulas I, II or III, or its corresponding enantiomer, diastereoisomer or tautomer, or pharmaceutically acceptable salt; and (b) a pharmaceutically acceptable carrier.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications.

Compounds of the invention intended for pharmaceutical use may be administered as crystalline or amorphous products. Pharmaceutically acceptable compositions include solid, semi-solid, liquid and aerosol dosage forms, such as, e.g., tablets, capsules, powders, liquids, suspensions, suppositories, aerosols or the like. They may be obtained, for example, as films by methods such as precipitation, crystallization, freeze drying, spray drying, or evaporative drying. Microwave or radio frequency drying may be used for this purpose. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like. The term "excipient" is used herein to describe any ingredient other than the compound(s) of the invention. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds of the formulae described herein. Dosage forms or compositions containing a compound as described herein in the range of 0.005% to 100% with the balance made up from non-toxic carrier may be prepared. The contemplated compositions may contain 0.001%-100% active ingredient, in one embodiment 0.1-95%, in another embodiment 75-85%. Actual methods of preparing such dosage forms are known, or will be apparent, to those skilled in this art; for example, see *Remington: The Science and Practice of Pharmacy*, 21st Edition (Lippincott Williams & Wilkins. 2005).

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule. Unit dosage forms in which the two active ingredients are physically separated are also contemplated; e.g., capsules with granules of each drug; two-layer tablets; two-compartment gel caps, etc.

In another preferred embodiment, compositions described herein are used as a drug-eluting coatings for a medical device including, but not limited to temporary or permanent implants, sponge, polymer, or gel.

The implant according to an embodiment of the invention is an orthopedic implant including, but not limited to (i) a hip joint, (ii) screws, cannulated screws, nails, meshs, cages, wires, pins, intramedullary nails, rods, posts, anchors, and plates intended to join or attach bone fragments, pieces, or parts with each other, (iii) external skeletal fixators such as monolateral, multiplanar or hybrid fixators, (iv) implants intended for treatment of degenerative instabilities, fractures, tumors, and deformities in respect of the spine, (v) craniomaxillofacial implants intended for treatment of fractures, reconstruction, and correction of deformities, of mandible, mid-face, or skull, (vi) surgical stents, collagen stents, intramedullary bone stents, (vii) anterior cruciate ligament (ACL) and posterior cruciate ligament (PCL) Reconstruction Systems, (viii) dental implants.

In some instances, a compound according to Formulas I, II or III is administered in combination with one or more therapeutic agents, e.g., therapeutic agents useful in the treatment of bone disorders or conditions described herein. For example, certain second therapeutic agents can promote tissue growth or infiltration, such as growth factors. Exemplary growth factors for this purpose include, without limitation, epidermal growth factor (EGF), vascular endothelial growth factor (VEGF), fibroblast growth factor (FGF), platelet-derived growth factor (PDGF), transforming growth factors (TGFs), parathyroid hormone (PTH), leukemia inhibitory factor (LIF), and insulin-like growth factors (IGFs). Other second therapeutic agents can promote bone growth, such as bone morphogenetic proteins (U.S. Pat. No. 4,761,471; PCT Pub. WO 90/11366), osteogenin (Sampath, et al., *Proc. Natl. Acad. Sci. USA* (1987), 84(20), 7109-7113), NaF (Tencer, et al., *Journal of Biomedical Materials Research* (1989), 23(6), 571-589), Peptide sequences such as IKVAV may be added to attach nerves and have those nerves express neuritis (Tashiro, et al., *The Journal of Biological Chemistry* (1989), 264(27), 16174-16182).

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid, which will be subsequently diluted to the above percentages. In some embodiments, the composition will comprise 0.2-2% of the active agent in solution.

It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Solid compositions can be provided in various different types of dosage forms, depending on the physicochemical properties of the drug, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided above, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of osteoporosis and osteoarthropathy; osteogenesis imperfecta, bone defects, bone fractures, periodontal disease, otosclerosis, wound healing, craniofacial defects, oncolytic bone disease, traumatic brain injuries related to the differentiation and development of the central nervous system, comprising Parkinson's disease, strokes, ischemic cerebral disease, epilepsy, Alzheimer's disease, depression, bipolar disorder, schizophrenia; eye diseases such as age related macular degeneration, diabetic macular edema, familial exudative vitreoretinopathy or retinitis pigmentosa and diseases related to differentiation and growth of stem cell, comprising hair loss, hematopoiesis related diseases, tissue regeneration related diseases and other diseases associated with abnormalities in development, stem cell differentiation and cell proliferation.

The actual dose of the active compounds of the present invention depends on the specific compound, and on the condition to be treated; the selection of the appropriate dose is well within the knowledge of the skilled artisan.

Methods of Treatment

The compounds and compositions provided herein can be used as activators of one or more members of the Wnt pathway, including one or more Wnt proteins, and thus can be used to treat a variety of disorders and diseases in which aberrant Wnt signaling is implicated, such as osteoporosis and osteoarthropathy; osteogenesis imperfecta, bone defects, bone fractures, periodontal disease, otosclerosis, wound healing, craniofacial defects, oncolytic bone disease, traumatic brain injuries related to the differentiation and development of the central nervous system, comprising Parkinson's disease, strokes, ischemic cerebral disease, epilepsy, Alzheimer's disease, depression, bipolar disorder, schizophrenia; eye diseases such as age related macular degeneration, diabetic macular edema, familial exudative vitreoretinopathy or retinitis pigmentosa and diseases related to differentiation and growth of stem cell, comprising hair loss, hematopoiesis related diseases, tissue regeneration related diseases and other diseases associated with abnormalities in development, stem cell differentiation and cell proliferation.

With respect to hair loss, the canonical Wnt/β-catenin signaling pathway is known to regulate hair follicle development and regeneration. In the epidermis, hair follicle development is initiated when mesenchymal cells populate the skin. During this process, signals emanating from the dermis induce epithelium thickening, elongation of the epithelial cells, and the formation of placodes containing Wnt-responsive cells. In response, placodes signal dermal cells to condense, thereby forming the dermal papilla component of the hair follicle, which is also responsive to Wnt signaling. Wnt3a is secreted from hair epithelium and acts in an autocrine and paracrine fashion, and it has been demonstrated that Wnt-3a maintains anagen gene expression in dermal papilla cells and mediates hair-inductive activity in an organ culture. This Wnt-3a-mediated hair growth might depend on the canonical Wnt/β-catenin signaling pathway because deletion of β-catenin or the Lef1 gene resulted in hair loss in mice. Accordingly, the compounds and compositions described herein may be used topically to treat hair loss by modulation of the Wnt/β-catenin signaling pathway.

With respect to neurodegenerative diseases, Wnt/β-catenin signal transduction system plays a crucial role in the differentiation and development of nerve cells for the central nervous system. Particularly, it is found that Wnt/β-catenin signaling is related to diseases resulting from the abnormality of nerve cells.

More particularly in Alzheimer's disease, studies indicate that a sustained loss of Wnt signaling function may be involved in the Aβ-dependent neurodegeneration observed in Alzheimer's brain. Consequently, the compounds and compositions described herein may be used to reactivate lost Wnt signaling function involved in neurodegeneration.

Other neurodegenerative diseases can also be treated with the compounds and compositions described herein.

More particularly, neurodegenerative diseases that may be treated by the compound, compositions and methods described herein include, but are not limited to, the following:

Parkinson's disease, schizophrenia, Huntington's disease, amyotrophic lateral sclerosis (Lou Gehrig's disease), primary lateral sclerosis (PLS), progressive muscular atrophy (PMA), bipolar disorder, depression, strokes, ischemic cerebral disease, epilepsy, brain damage and spinocerebellar ataxia type 1 (SCA1).

With respect to eye diseases, Wnt/β-catenin signal transduction system regulates the maintenance of a retinal progenitor population in the ciliary marginal zone (CMZ), and thus function as a putative stem cell factor in the retina. Particularly, it is found that Wnt/β catenin pathways mediate a process of retinal repair and that application of Wnt activators may promote retinal neuron regeneration. In the setting of injury, Wnts may serve a protective role. It has been recently shown that Wnt3a protects photoreceptors. The results of this study may well be interpreted as an upregulation of self-renewal of stem cells in the setting of injury.

Accordingly, the compounds and compositions described herein may be used to enhance replacement of lost neurons caused by disease and protect photoreceptors during injury by modulation of the Wnt/β-catenin signaling pathway.

Other eye diseases can also be treated with the compounds and compositions described herein.

More particularly, eye diseases that may be treated by the compound, compositions and methods described herein include, but are not limited to, the following:

Age related macular degeneration, diabetic macular edema, familial exudative vitreoretinopathy and retinitis pigmentosa.

With respect to diseases associated with differentiation and growth of stem cell, Wnt/β-catenin signaling is critical in the self-renewal of stem cells in many different tissues, including the skin, intestine, brain and blood. Therefore, the compounds and compositions described herein may be used to treat disorders and diseases related to abnormalities in development.

Evaluation of Biological Activity

The biological activity of the compounds described herein can be tested using any suitable assay known to those of skill in the art, e.g., WO 2001/053268 or WO 2005/009997. For example, the activity of a compound may be tested using one or more of the test methods outlined below.

Example 7

Compounds that enhance the Wnt activity, or Activators, were assayed as follows. Reporter cell lines were generated by stably transducing cells of cancer cell lines (e.g., colon cancer) with a lentiviral construct that include a wnt-responsive promoter driving expression of the firefly luciferase gene.

Lentiviral constructs were made in which the SP5 promoter, a promoter having eight TCF/LEF binding sites derived from the SP5 promoter, is linked upstream of the firefly luciferase gene. The lentiviral constructs can also include a hygromycin resistance gene as a selectable marker. The SP5 promoter construct were used to transduce SW480 cells, a colon cancer cell line having a mutated APC gene that generates a truncated APC protein, leading to de-regulated accumulation of β-catenin.

Cultured SW480 cells bearing a reporter construct can be distributed at approximately 10,000 cells per well into 384 or 96 well multiwell plates. Compounds from a small molecule compound library can then be added to the wells in half-log dilutions using three or ten micromolar top concentration. A series of control wells for each cell type received only buffer and compound solvent DMSO. Twenty-four hours after the addition of compound, reporter activity for luciferase can be assayed, for example, by addition of the BrightGlo luminescence reagent (Promega) and the Victor3 plate reader (Perkin Elmer). Readings are normalized to DMSO only treated cells, and any activities above DMSO are considered activation. Compounds are considered activators if reporter activities are 2× fold or greater than DMSO. $EC_{50}$ is the concentration at half maximal activation. Table 2 shows the activity of selected activators.

TABLE 2

| Compound | Wnt activation, $IC_{50}$ |
|---|---|
| 1 | 0.028-0.029 μM |
| 2 | 0.013 μM |
| 3 | 0.036-0.041 μM |
| 4 | 0.61-1.0 μM |
| 5 | 0.64-1.9 μM |
| 6 | 2.1 μM |
| 7 | 0.096-0.27 μM |
| 8 | 0.083 μM |
| 9 | >10 μM |
| 10 | >10 μM |
| 11 | >10 μM |
| 12 | >10 μM |
| 14 | >10 μM |
| 15 | 0.68-2.1 μM |
| 16 | 2.57 μM |
| 17 | >10 μM |
| 18 | 6.0 μM |
| 19 | 2.8-5.0 μM |

The term "comprising" as used herein is synonymous with "including," "containing," or "characterized by," and is inclusive or open-ended and does not exclude additional, unrecited elements or method steps.

What is claimed is:

1. A compound or pharmaceutically acceptable salt thereof having the structure of Formula I:

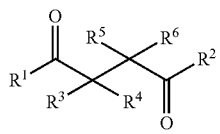

wherein $R^1$ is a substituted or unsubstituted heteroaryl, wherein the heteroaryl is selected from the group consisting of

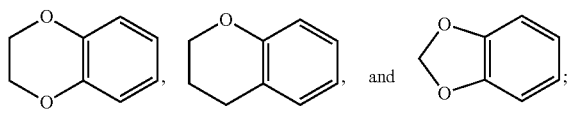

with the proviso that a carbon atom of the $R^1$ heteroaryl is attached to the carbonyl;
$R^2$ is a substituted or unsubstituted aryl, wherein the aryl is selected from phenyl or naphthyl; and
$R^3$, $R^4$, $R^5$ and $R^6$ are H.

2. The compound of claim 1 having a structure selected from the group consisting of:

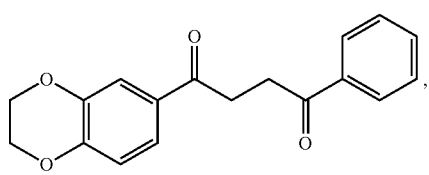

-continued

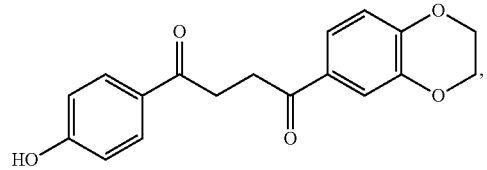

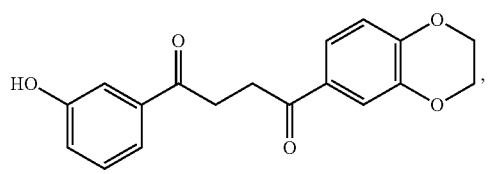

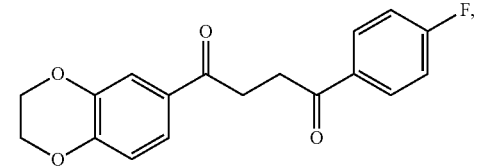

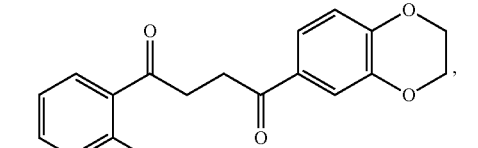

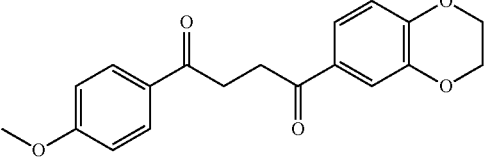

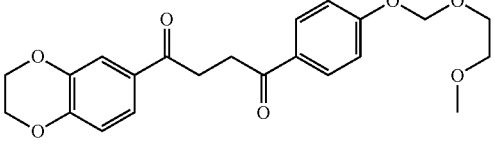

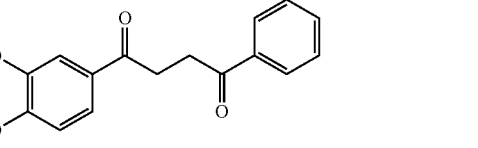

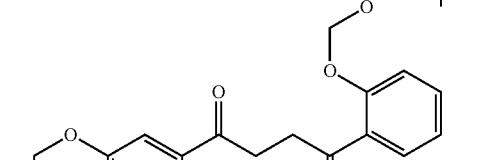

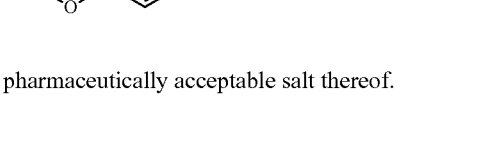

or a pharmaceutically acceptable salt thereof.

3. The compound of claim 1, wherein $R^1$ is

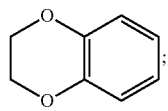

and $R^2$ a substituted or unsubstituted phenyl.

4. The compound of claim 3, wherein the compound of Formula I is:

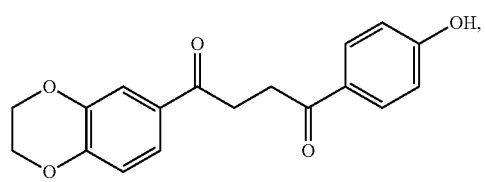 [SMILES: O=C(CCC(=O)c1ccc2c(c1)OCCO2)c1ccc(O)cc1]

or a pharmaceutically acceptable salt thereof.

5. The compound of claim 3, wherein the compound of Formula I is:

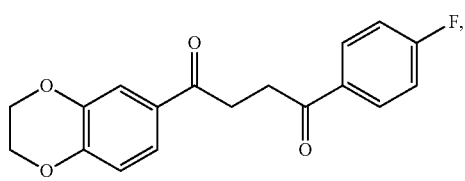 [SMILES: O=C(CCC(=O)c1ccc2c(c1)OCCO2)c1ccc(F)cc1]

or a pharmaceutically acceptable salt thereof.

6. The compound of claim 3, wherein the compound of Formula I is:

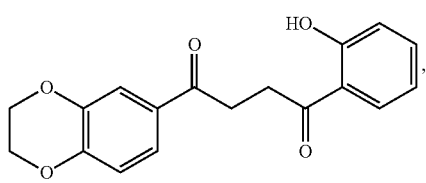 [SMILES: O=C(CCC(=O)c1ccccc1O)c1ccc2c(c1)OCCO2]

or a pharmaceutically acceptable salt thereof.

7. The compound of claim 1, wherein $R^1$ is

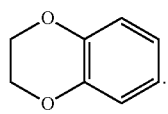

8. The compound of claim 1, wherein $R^2$ is a substituted or unsubstituted phenyl.

9. A pharmaceutical composition comprising a therapeutically effective amount of a compound or a pharmaceutically acceptable salt thereof having the structure of Formula I:

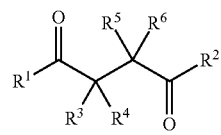

wherein $R^1$ is a substituted or unsubstituted heteroaryl, wherein the heteroaryl is selected from the group consisting of

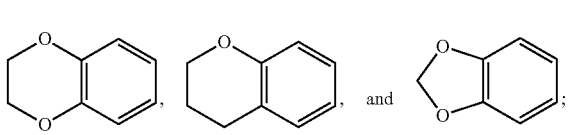

with the proviso that a carbon atom of the $R^1$ heteroaryl is attached to the carbonyl;

$R^2$ is a substituted or unsubstituted aryl, wherein the aryl is selected from phenyl or naphthyl; and $R^3$, $R^4$, $R^5$ and $R^6$ are H;

and a pharmaceutically acceptable excipient.

10. A pharmaceutical composition of claim 9, wherein $R^1$ is

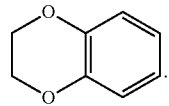

11. A pharmaceutical composition of claim 9, wherein $R^2$ is a substituted or unsubstituted phenyl.

12. A pharmaceutical composition of claim 9, wherein $R^1$ is

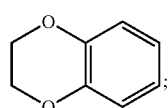

and $R^2$ is a substituted or unsubstituted phenyl.

13. A pharmaceutical composition of claim 9 having a structure selected from the group consisting of:

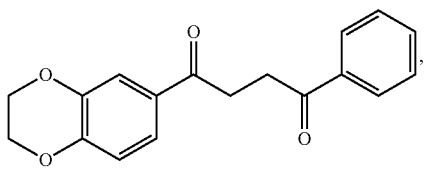

-continued

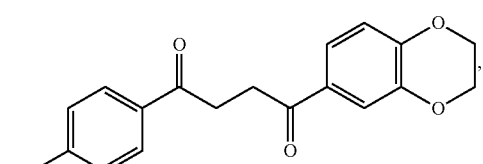

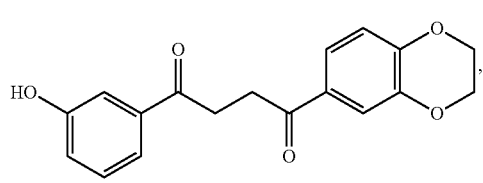

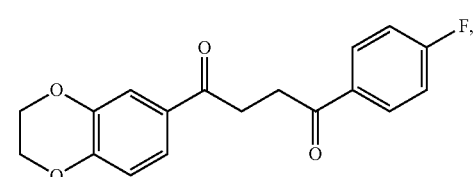

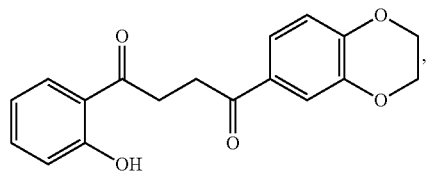

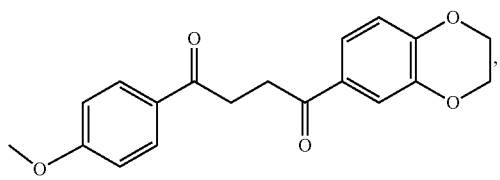

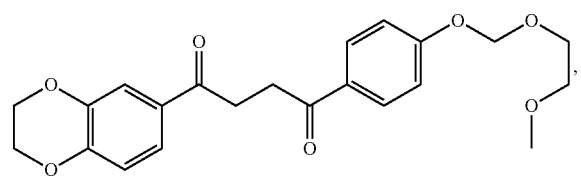

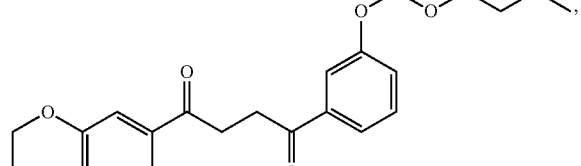

-continued and

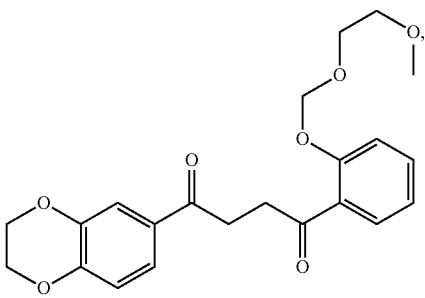

or a pharmaceutically acceptable salt thereof.

14. A pharmaceutical composition of claim 9, wherein the compound of Formula I is:

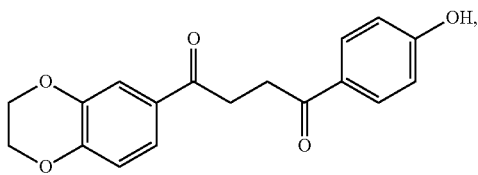 [SMILES: O=C(CCC(=O)c1ccc2c(c1)OCCO2)c1ccc(O)cc1]

or a pharmaceutically acceptable salt thereof.

15. A pharmaceutical composition of claim 9, wherein the compound of Formula I is:

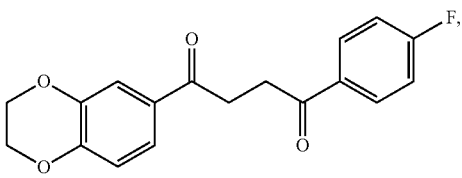 [SMILES: O=C(CCC(=O)c1ccc2c(c1)OCCO2)c1ccc(F)cc1]

or a pharmaceutically acceptable salt thereof.

16. A pharmaceutical composition of claim 9, wherein the compound of Formula I is:

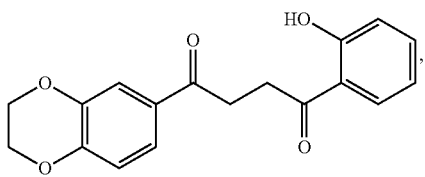 [SMILES: O=C(CCC(=O)c1ccccc1O)c1ccc2c(c1)OCCO2]

or a pharmaceutically acceptable salt thereof.

* * * * *